(12) United States Patent
Stromsoe

(10) Patent No.: US 10,018,611 B2
(45) Date of Patent: Jul. 10, 2018

(54) SOIL COMPACTION SYSTEM AND METHOD

(71) Applicant: Roger Arnold Stromsoe, Sandton (ZA)

(72) Inventor: Roger Arnold Stromsoe, Sandton (ZA)

( * ) Notice: Subject to any disclaimer, the term of this patent is extended or adjusted under 35 U.S.C. 154(b) by 92 days.

(21) Appl. No.: 14/779,876

(22) PCT Filed: Apr. 1, 2014

(86) PCT No.: PCT/IB2014/060350
§ 371 (c)(1),
(2) Date: Sep. 24, 2015

(87) PCT Pub. No.: WO2014/162261
PCT Pub. Date: Oct. 9, 2014

(65) Prior Publication Data
US 2016/0054283 A1    Feb. 25, 2016

(30) Foreign Application Priority Data
Apr. 2, 2013    (ZA) .................................. 2013/02370

(51) Int. Cl.
*E01C 19/30*    (2006.01)
*E01C 19/26*    (2006.01)
(Continued)

(52) U.S. Cl.
CPC ........... *G01N 33/24* (2013.01); *E01C 19/002* (2013.01); *E01C 19/235* (2013.01);
(Continued)

(58) Field of Classification Search
CPC ..... G01N 33/24; E01C 19/002; E01C 19/235; E01C 19/236; E01C 19/266;
(Continued)

(56) References Cited

U.S. PATENT DOCUMENTS

| | | | |
|---|---|---|---|
| 4,127,351 A | * | 11/1978 | Vural ........................ E02D 3/02 404/133.05 |
| 4,149,253 A | * | 4/1979 | Paar .......................... E02D 3/02 404/117 |

(Continued)

FOREIGN PATENT DOCUMENTS

| WO | 9627713 | | 9/1996 |
|---|---|---|---|
| WO | WO 97/04179 | * | 2/1997 |
| WO | 2007073451 A1 | | 6/2007 |

OTHER PUBLICATIONS

International Search Report from International Application No. PCT/IB2014/060350 dated Jul. 7, 2014.
(Continued)

*Primary Examiner* — Helen Kwok
(74) *Attorney, Agent, or Firm* — Meunier Carlin & Curfman LLC

(57) ABSTRACT

The invention relates to a method of, and system for, obtaining an indication of the soil strength of soil over which a compactor roller travels. The method includes determining the depth to which a drum of the compactor roller penetrates into and depresses the soil when the compactor roller travels over a soil surface. The system includes a compactor roller, a measuring arrangement and a processor which is operatively connected to the measuring arrangement and which is configured to process data received from the measuring arrangement. The measuring arrangement includes an inertial measurement unit which is operatively connected to the compactor roller, wherein the arrangement is configured to obtain an indication of the soil strength of soil over which the compactor roller travels during operation, by determining the depth to which the drum penetrates into and depresses the soil over which it travels.

20 Claims, 13 Drawing Sheets

(51) Int. Cl.
  *E01C 19/28* (2006.01)
  *E02D 3/02* (2006.01)
  *G01N 33/24* (2006.01)
  *E02D 1/02* (2006.01)
  *E02D 3/026* (2006.01)
  *E01C 19/23* (2006.01)
  *E01C 19/00* (2006.01)
  *G01B 21/18* (2006.01)

(52) U.S. Cl.
  CPC .......... *E01C 19/236* (2013.01); *E01C 19/266* (2013.01); *E01C 19/281* (2013.01); *E01C 19/288* (2013.01); *E02D 1/02* (2013.01); *E02D 1/022* (2013.01); *E02D 3/026* (2013.01); *G01B 21/18* (2013.01)

(58) Field of Classification Search
  CPC ...... E01C 19/281; E01C 19/288; E01C 19/26; E02D 1/02; E02D 1/022; E02D 3/026; E02D 3/039; E02D 3/02
  See application file for complete search history.

(56) References Cited

U.S. PATENT DOCUMENTS

| | | | | |
|---|---|---|---|---|
| 5,562,365 A * | 10/1996 | Berrange | ............. | E01C 19/235 |
| | | | | 172/777 |
| 6,004,076 A * | 12/1999 | Cook | ................. | E01C 19/235 |
| | | | | 318/128 |
| 6,065,904 A * | 5/2000 | Cook | ................. | E01C 19/235 |
| | | | | 404/117 |
| 6,382,873 B1 * | 5/2002 | Mulders | ............. | E01C 19/235 |
| | | | | 172/148 |
| 6,973,821 B2 * | 12/2005 | Corcoran | ............. | E02D 3/026 |
| | | | | 73/78 |
| 7,410,323 B1 * | 8/2008 | Roth | ................. | E01C 19/235 |
| | | | | 404/132 |
| 7,428,455 B2 * | 9/2008 | Corcoran | ............. | E01C 19/288 |
| | | | | 404/125 |
| 7,614,821 B2 * | 11/2009 | Stromsoe | ............. | E02D 3/026 |
| | | | | 404/126 |
| 8,190,338 B2 * | 5/2012 | Commuri | ............. | E01C 19/288 |
| | | | | 701/50 |
| 9,169,605 B2 * | 10/2015 | Corcoran | ............. | E01C 19/26 |
| 9,534,995 B2 * | 1/2017 | Stoeckel | ................. | G01N 3/08 |
| 2005/0194154 A1 * | 9/2005 | Hester | ................. | E02D 3/026 |
| | | | | 172/1 |
| 2007/0150147 A1 * | 6/2007 | Rasmussen | ............. | E01C 19/004 |
| | | | | 701/50 |
| 2008/0008542 A1 | 1/2008 | Stromsoe et al. | | |
| 2008/0063473 A1 * | 3/2008 | Congdon | ............. | E01C 19/288 |
| | | | | 404/75 |
| 2012/0048160 A1 * | 3/2012 | Adams | ................. | A01C 7/203 |
| | | | | 111/163 |
| 2012/0107045 A1 * | 5/2012 | DeClerk | ............. | E01C 19/236 |
| | | | | 404/75 |
| 2012/0144704 A1 * | 6/2012 | Cone | ................. | E02F 3/6481 |
| | | | | 37/413 |
| 2013/0046419 A1 * | 2/2013 | Anderson | ............. | E02F 9/2054 |
| | | | | 701/2 |
| 2013/0180742 A1 * | 7/2013 | Wendte | ................. | A01B 63/008 |
| | | | | 172/4 |
| 2014/0048296 A1 * | 2/2014 | Bassett | ................. | A01B 71/02 |
| | | | | 172/4 |
| 2014/0236431 A1 * | 8/2014 | Hendrickson | ........ | A01B 79/005 |
| | | | | 701/50 |
| 2015/0241333 A1 * | 8/2015 | Pistrol | ................. | E01C 19/23 |
| | | | | 73/9 |
| 2015/0362414 A1 * | 12/2015 | Stoeckel | ................. | G01N 3/08 |
| | | | | 404/128 |

OTHER PUBLICATIONS

Extended Search Report issued in European Application No. 14778655.2, dated Jan. 24, 2017.
Office Action issued in Chinese Application No. 201480029708.8, dated Mar. 20, 2017.
Office Action issued in Chinese Application No. 201480029708.8, dated Oct. 11, 2016.

* cited by examiner

SOIL COMPACTION SYSTEM AND METHOD

FIELD OF INVENTION

THIS INVENTION relates to a soil compaction method and system, as well as to a compactor roller.

BACKGROUND OF INVENTION

The term "impact compactor" or "impact roller" typically refers to a soil compaction device which includes one/two compactor drums of non-round shape which, when towed/driven over a soil surface, produces a series of periodic impact blows on the soil surface (see FIG. 1). These periodic blows compact the soil which results in packing and orientating the soil into a more dense and effective particle arrangement, which reduces air voids and prevents further densification and shear failure of the soil. The compactor drums of the impact compactor each has a series of spaced apart salient points on its periphery with each such salient point followed by a compacting face. As the impact compactor is towed over the soil surface, for instance by means of a tractor, the compactor drum rises up on each salient point and then falls forwardly and downwardly as it passes over that point, with the result that the following compacting face applies an impact blow to the soil surface (see FIG. 2). The function of the compactor drum is therefore to store potential energy as it rises up on each salient point and then to deliver this energy as an impact blow.

In order to achieve the required degree of compaction, a predetermined number of passes is normally applied by the impact compactor to the site. After the predetermined number of passes has been carried out, soil tests are conducted at isolated discrete positions in order to establish whether the required degree of compaction has been achieved. Although these soil tests are only conducted on a very small ratio of the total area undergoing compaction (usually no more than one in one hundred thousandths of the area being compacted) the test results are extrapolated to indicate whether the soil has reached the required degree of compaction; still requires further passes of the impact compactor; or has already exceeded the required degree of compaction. It is therefore often incorrectly assumed that the site has been adequately compacted when in fact portions of the site remain inadequately compacted. Poorly compacted soil can result in costly premature failure of whatever road, railway line, airport runway or other structure the soil may in future be required to carry.

Impact compactors have proved to work well in achieving high levels of soil compaction, even at substantial depths below the soil surface. This allows for the achievement of greatly improved uniformity of soil strength over a site, provided that the entire site is rolled to refusal or near refusal of settlement. However, it is difficult to determine when refusal of settlement has been reached over an entire work site as some areas may reach refusal of settlement earlier than others, resulting in insufficient or superfluous compaction over large areas of the work site. Different soil types may have different elastic properties once refusal of settlement has been achieved and it is therefore important to measure these elastic properties to ensure uniformity of the achieved soil strength.

It can be shown that the amount by which the drum of the impact compactor penetrates into the soil during an impact blow is directly related to the soil strength. Large penetration measurements would correlate to low soil strength and small penetration measurements would correlate to high soil strength. Once the soil refuses further settlement, the penetration measurements achieved will remain constant, indicating that any deformation of the soil achieved is elastic. Elastic deformation occurs when there is a temporary change in the shape of the soil which is fully recovered when the applied stress (the compactor drum) is removed. The response of the soil to unload is immediate. Plastic deformation occurs when there is a permanent change in the shape of the soil which is not recovered when the applied stress is removed. When there is no more plastic deformation during an impact blow, it means that the impact compactor has reached the limit of its compaction capability and cannot improve the soil strength any further. It can be said that the soil reaction force has reached a form of equilibrium with the pressure applied by the falling compactor drums.

The effect which the compactor drums (due to their shape) have on a ground surface over which they travel can be visually illustrated as shown in FIG. 3, with the ground forming a sinusoidal pattern. The upper sinusoidal wave in FIG. 3 illustrates the pattern formed on the first pass where the depth of penetration may be as great as 150 mm or more. The middle and lower waves illustrate how the amplitude of the sinusoidal wave reduces as the impact compactor completes more passes and the ground gets harder. The impact compactor, however, does not deliver an impact blow to the same spot every time and the sinusoidal patterns of each pass will therefore overlap.

Soil density is extensively used by the construction industry to specify, estimate, measure, and control soil compaction even though it is not usually the most relevant engineering property for determining whether the ground is well compacted. This practice was adopted long ago because soil density could be easily determined from measurements using devices such as a nuclear density gauge which is commonly used today.

Current methods for measuring soil strength are relatively slow, labour-intensive and/or lack accuracy. Construction sites are often under sampled, causing inadequate compaction to go undetected or feedback to be provided too late for the cost-effective correction of any problems.

It is an aim of the present invention to provide means which will at least alleviate some of the above-identified problems.

SUMMARY OF INVENTION

In accordance with the invention there is provided a method of obtaining an indication of the soil strength of soil over which a compactor roller travels, the method including:
  determining the depth to which a drum of the compactor roller penetrates into and depresses the soil when the compactor roller travels over a soil surface.

It is important to bear in mind that for the purposes of this specification, when terms such as "measuring", "calculating" and "determining" are used with reference to a specific value/amount, it does not necessarily refer to the actual specific value/amount, but may also refer to an estimation thereof.

The term "compactor roller" should be interpreted to include a so-called impact compactor or impact roller.

The compactor roller may be an impact compactor.

A compactor roller typically includes at least one drum/roller which compacts the ground over which the compactor roller travels by delivering periodic impact blows. For the sake of clarity the term "drum" will be used in this context instead of "roller".

The depth to which a drum of a compactor roller penetrates into and depresses the soil may be referred to as the stroke depth.

The measurement of soil strength is used to determine how strong the soil is, how capable it is of carrying a load and whether or not it is compacted within certain pre-defined specifications. The invention provides different, but interrelated, methods or measurement techniques which can be used to determine, estimate or provide an indication of soil strength. An indication of the soil strength may be obtained by:
  using the stroke depth only (as described above);
  using the stroke depth together/in conjunction with dynamic data related to the displacement of the drum of the compactor roller as it travels over the soil and correlating the dynamic data to a scale which indicates the soil strength based on the particular dynamic data; or
  using the stroke depth to measure/determine one (or more) of the following measurements/estimations:
    the bearing capacity of the soil over which the impact compactor travels during operation;
    the so-called K-value of the soil over which the impact compactor travels during operation;
    the soil modulus of the soil over which the impact compactor travels during operation; or
    the energy absorbed by the soil during an impact blow.

Bearing capacity, K-value, soil modulus and the energy referred to above are well known terms which are used in the field of impact compaction and can be used to provide an indication of soil strength. The measurements/estimation of the bearing capacity, K-value, soil modulus and energy (referred to above) may be referred to as the direct measurements of soil strength.

The method may therefore include:
  measuring/determining the bearing capacity of the soil over which the impact compactor travels during operation;
  measuring/determining the so-called K-value of the soil over which the impact compactor travels during operation;
  measuring/determining the soil modulus of the soil over which the impact compactor travels during operation; or
  measuring/determining the energy absorbed by the soil during an impact blow.

The step of determining the depth to which the drum penetrates into and depresses the soil (stroke depth) may include measuring the amount of relative displacement between:
  a drum of the impact compactor, or a mounting arrangement of the impact compactor which displaceably mounts the drum to a chassis structure of the impact compactor, and
  a reference/datum point.

The reference/datum point may be the chassis structure or part of the impact compactor which is unaffected by the displacement of the drum relative to the chassis structure (i.e. a part which is fixed relative to the chassis structure).

The step of determining the depth to which the drum penetrates into and depresses the soil may include measuring the distance between:
  an axle assembly of the impact compactor on which the drum is mounted, or a drag link via which the axle assembly is mounted to the chassis structure, wherein the axle assembly and the drag link form part of the mounting arrangement; and
  the chassis structure.

The distance may be a vertical distance. The measuring of the distance may be by means of a distance measuring device.

The distance measuring device may include:
  at least one laser, infra-red or ultrasonic sensors;
  a linear potentiometer; and/or
  a linear encoder;

The distance measuring device may include two laser, infra-red and/or ultrasonic sensors.

A mounting arrangement of the impact compactor on which a drum of the impact compactor is mounted and which displaceably mounts the drum to a chassis structure of the impact compactor, may include one or more hinged/pivotal connections via which the drum is connected to the chassis structure of the impact compactor, and the method may include monitoring the relative angular displacement between two hingidly connected parts of one, or each, of the hinged/pivotal connections.

The impact compactor may include a chassis structure, a drag link, at least one impact drum of non-round shape which is rotatably mounted to the drag link, and a link (hereinafter referred to as the "drop link") via which the drag link is connected to the chassis structure, wherein the drop link is pivotally/hingidly connected to both the chassis structure and the drag link at spaced apart positions, and wherein the drop link and drag link form part of a drum mounting arrangement, wherein the method may include:
  measuring the relative angular displacement between the drag link and the drop link; and/or the drop link and the chassis structure, with the change in angular displacement being indicative of the amount of relative displacement between the impact drum and the chassis structure, which, in turn, is indicative of the depth to which a drum of the compactor roller penetrates into and depresses the soil The method may include using the known lengths of the drop link and drag link together with data obtained from measuring the relative angular displacement(s) in order to obtain an indication of the amount of relative displacement between the impact drum and the chassis structure.

The measuring of the relative angular displacement may be by means of a gyroscope, an inertial measurement unit (hereinafter referred to as "IMU"), an optical flow sensor and/or a rotary encoder.

In an alternative embodiment, the step of determining the depth to which the drum penetrates into and depresses the soil may include:
  measuring the pressure in a cylinder of a pneumatic piston-cylinder device which is operatively connected between
    a mounting arrangement of the impact compactor on which a drum of the compactor roller is mounted and which displaceably mounts the drum to a chassis structure of the impact compactor, and
    the chassis structure, and
  deriving an indication of the amount of relative displacement between the drum and the chassis structure from the measured pressure.

In an alternative embodiment, the step of determining the depth to which the drum penetrates into and depresses the soil may include:
  measuring the amount of acceleration (i.e. a change in speed) which a drum of the compactor roller is subjected to during an impact blow; and
  deriving an indication of the amount of relative displacement between the drum and a chassis structure of the impact compactor to which the drum is displaceably mounted from the measured acceleration.

The step of deriving an indication of the amount of relative displacement from the measured acceleration may include double integrating data obtained from the measuring of the acceleration with respect to time, in order to determine the amount of displacement.

The acceleration may be the vertical acceleration.

The method may include extracting a vertical component of data obtained from the measuring of the acceleration of the drum in order to derive an indication of the amount of relative vertical displacement between the drum and the chassis structure.

The measuring of the acceleration may be by means of an accelerometer. The accelerometer may be mounted on the drum or a mounting arrangement of the impact compactor on which the drum is mounted and which displaceably mounts the drum to a chassis structure of the impact compactor.

The step of determining the depth to which the drum penetrates into and depresses the soil may be conducted continuously/continually (i.e. in real time). More specifically, the method may include continuously/continually sending a signal, which is indicative of the soil strength, to a processor, as the impact compactor travels over and along an upper surface of the soil.

The step of determining the depth to which a drum of the impact compactor penetrates into and depresses the soil when the impact compactor travels over a soil surface may include:
    obtaining data from an IMU which is mounted on a drum of the impact compactor or a mounting arrangement on which the drum is mounted and which displaceably mounts the drum to a chassis structure of the impact compactor, and
    determining the penetration depth by using the data.

The step of determining the depth to which a drum of the impact compactor penetrates into and depresses the soil when the impact compactor travels over a soil may include:
    determining a vertical component of acceleration data obtained from the IMU.

The method may include double integrating the vertical component of the acceleration data with respect to time.

The step of determining the depth to which a drum of the impact compactor penetrates into and depresses the soil when the impact compactor travels over a soil may include measuring the vertical positions of a point on the chassis structure and a point on the drum or the drum mounting arrangement by using two RTK GNSS (Real Time Kinematic Global Navigation Satellite System) devices mounted at those points; and calculating the difference between the two vertical positions measured by the two devices. Alternatively a simple GPS or equivalent device can be used instead of the RTK GNSS device, although this might be less accurate.

The method may include:
    calculating the amount of force applied by the drum of the impact compactor to the soil during an impact blow; and
    calculating a contact area between the drum and the soil.

The step of calculating the amount of force applied by the drum may include using acceleration data obtained from the IMU and a kinematic model of the impact compactor. More specifically, the step may include calculating the amount of force using Newton's 2nd law.

The step of calculating the amount of force applied by the drum may include calculating the peak force which the drum applied to the soil during an impact blow.

The step of calculating the force applied by the drum may include calculating the energy absorbed by the soil during an impact blow of the drum of the impact compactor.

The method may include using the following measurements to calculate the amount of energy:
    the change in height of the drum;
    the change in rotational speed of the drum and/or the drag link; and/or
    a deflection of an axle assembly of the mounting arrangement on which the drum is mounted, relative to drum damping rubbers which are mounted between the axle assembly and the drum.

The force applied by the drum during an impact blow may be calculated using the mathematical equation:

$$\Delta E = \int F dx$$

Assuming a constant force over each small time step, the average force may be calculated from:

$$\Delta E = F_{avg} x$$

The step of calculating the force applied by the drum may include the following step:
    determining the position of the drum of the impact compactor when a drum impact surface of the drum starts to make contact with the soil during an impact blow.

The step of determining the position of the drum when a drum impact surface of the drum starts to make contact with the soil during an impact blow may include determining the position at which the drum starts to decelerate during an impact blow. One type of impact compactor includes a chassis structure, a drag link, at least one impact drum which is rotatably mounted to the drag link, and a link (hereinafter referred to as the "drop link") via which the drag link is connected to the chassis structure, wherein the drop link is pivotally/hingidly connected to both the chassis structure and the drag link at spaced apart positions, and wherein the drop link and drag link form part of a drum mounting arrangement.

Alternatively, the step of determining the position of the drum when a drum impact surface of the drum starts to make contact with the soil during an impact blow may include:
    determining when the drum impact surface makes contact with the soil by using a sensor which is mounted on the drum, chassis structure or the drum mounting arrangement, and which is configured to detect when the drum impact strikes the soil during an impact blow.

The sensor may be:
    a microphone which is configured to detect/identify the sound created when the drum strikes the soil during an impact blow
    a strain gauge;
    a contact sensor;
    a pressure sensor; or
    a capacitive electrode which is configured to sense the presence of the soil.

The calculation of the contact area may include the following steps:
    calculating the rotational angle of the drum relative to gravity (i.e. a vertically downward direction); and
    inserting measurements obtained from the above step, as well as the step of determining the penetration depth, into a mathematical equation.

The step of calculating the rotational angle of the drum relative to gravity may include using accelerometer and gyroscope data obtained from the IMU in order to calculate the rotational angle.

The contact area may be a function of the rotational angle of the drum, the drum profile and stroke depth.

The method may include measuring bearing capacity of soil over which an impact compactor travels during operation, wherein the step of measuring bearing capacity includes:
  determining a peak force applied by a drum of the impact compactor to the soil during an impact blow;
  determining a contact area between the drum and the soil at the peak force; and
  calculating the bearing pressure by dividing the peak force by the contact area.

Bearing capacity refers to the relationship between the bearing pressure and the stroke depth. More specifically, bearing capacity refers to the relationship between the continuous bearing pressure and stroke depth data. Bearing capacity can therefore be derived from a graph which plots bearing pressure versus stroke depth.

The calculation of the bearing capacity may be done continuously/continually as the impact compactor travels over the soil.

The step of measuring bearing capacity may include:
  determining an instantaneous bearing pressure applied by the drum on the soil;
  and
  providing a graphical illustration of the pressure applied versus the depth of penetration of the drum into the soil.

The method may further include calculating a safe, allowable and/or ultimate bearing capacity of the soil using data obtained from the determination of the pressure applied by the drum and the depth of penetration of the drum into the soil. More specifically, the safe, allowable and/or ultimate bearing capacity of the soil may be calculated using the graphical illustration of the pressure applied versus the measurement of the penetration of the drum into the soil.

The method may include measuring a K-value of soil over which an impact compactor travels during operation, wherein the step of measuring the K-value includes:
  determining an instantaneous pressure applied by a drum of the impact compactor on the soil during an impact blow;
  calculating the K-value using data obtained from the pressure applied by the drum and the depth of penetration of the drum into the soil.

The step of measuring the K-value may include providing a graphical illustration of the pressure applied versus the depth of penetration of the drum into the soil. The method may therefore include calculating a K-value for a specific applied pressure using the graphical illustration of the pressure applied versus the measurement of the penetration of the drum into the soil.

The method may include measuring a soil modulus of soil over which an impact compactor travels during operation, wherein the step of measuring a soil modulus includes:
  determining the ratio of pressure applied by the drum during an impact blow to strain which the drum, and/or or a mounting arrangement of the impact compactor on which the drum is mounted and which displaceably mounts the drum to a chassis structure of the impact compactor, are subjected to during operation.

The step of measuring a soil modulus may include:
  calculating the modulus using Boussinesq's mathematical equation for a circular plate:

$$\Delta z = \frac{\pi P a}{2E}(1 - v^2),$$

where P is the pressure applied, v is Poisson's ratio, $\Delta z$ is the depth to which the drum of the compactor roller penetrates into and depresses the soil, a is a contact area between the drum and the soil and E is the modulus; and
  finding an empirical correlation that will adjust the modulus for the drum shape.

The calculations/estimations referred to above may be performed by a processor.

In accordance with another aspect of the invention there is provided a compactor roller which includes:
  a chassis structure;
  at least one drum which is rotatably mounted to the chassis structure by means of a drum mounting arrangement, wherein the drum mounting arrangement is configured to allow displacement of the at least one drum relative to the chassis structure such that the at least one drum can be displaced upwardly and downwardly relative to the chassis structure as the compactor roller travels along a ground surface; and
  a measuring arrangement, which is operatively connected to the chassis structure and/or the drum mounting arrangement, and which is configured to obtain an indication of the soil strength of soil over which a compactor roller travels when the compactor roller travels over a soil surface, by determining the depth to which the at least one drum penetrates into and depresses the ground over which it travels during operation.

The compactor roller may be an impact compactor.

The compactor roller may include an inertial measurement unit (hereinafter referred to as "IMU") which is mounted on the drum or the drum mounting arrangement.

The compactor roller may include an attitude filter which is operatively connected to, or forms an integral part of, the IMU, which is configured to reduce electronic noise of readings received from components which form part of the IMU in order to help increase the accuracy and/or reliability of the readings. The filter may be a complementary filter or a Kalman filter.

The compactor roller may include an inertial navigation system (hereinafter referred to as "INS") which is operatively connected to the IMU or of which the IMU forms an integral part of. The INS may be configured to calculate the position of the IMU, and therefore also that part of the compactor roller on which it is mounted, i.e. the drum or the mounting arrangement.

The measuring arrangement may include at least one distance measuring device which is:
  mounted on the drum mounting arrangement and directed towards the chassis structure or part of the compactor roller which is unaffected by the displacement of the at least one drum relative to the chassis structure (i.e. a part which is fixed relative to the chassis structure); or
  mounted on the chassis structure or part of the compactor roller which is unaffected by the displacement of the at least one drum relative to the chassis structure and directed towards the drum or the drum mounting arrangement.

The distance measuring device may include:
  a laser sensor; an infra-red sensor; or an ultrasonic sensor which is adapted to sense distance;
  a linear potentiometer; and/or a linear encoder.

The sensor may be substantially vertically oriented so that it can sense the vertical distance between that part of the compactor roller to which the sensor is mounted (e.g. the mounting arrangement) and the part of the compactor roller towards which it is directed (e.g. the chassis structure).

The drum mounting arrangement may include a drag link which is pivotally/hingidly mounted to the chassis structure and an axle assembly which mounts the at least one drum rotatably to the drag link, and wherein the sensor is mounted on the drag link or axle assembly and directed towards the chassis structure.

The drum mounting arrangement may include a drag link which is pivotally/hingidly mounted to the chassis structure and an axle assembly which mounts the at least one drum rotatably to the drag link, and wherein the measuring arrangement includes two distance measuring devices, wherein the one distance measuring device is mounted on the drag link and directed towards the chassis structure and the other distance measuring device is mounted on the axle assembly and directed towards the chassis structure.

The distance measuring devices may be obliquely angled relative to each other.

In an alternative embodiment, the measuring arrangement may include:
  a piston-cylinder device which is operatively connected between:
    the drum mounting arrangement; and
    the chassis structure or part of the compactor roller which is unaffected by the displacement of the at least one drum relative to the chassis structure; and
  a pressure meter which is operatively connected to the piston-cylinder device in order to measure the pressure inside a cylinder of the piston-cylinder device,
wherein the changes in pressure inside the cylinder is indicative of the amount of relative displacement between the at least one drum and the chassis structure.

The piston-cylinder device may be a pneumatic or hydraulic piston-cylinder device.

In another alternative embodiment, the measuring arrangement may include at least one angle measurement device which is operatively mounted between:
  the chassis structure or part of the compactor roller which is unaffected by the displacement of the at least one drum relative to the chassis structure; and
  the drum mounting arrangement,
wherein the amount of relative angular displacement detected by the angle measurement device is indicative of the amount of relative displacement between the at least one drum and the chassis structure.

The impact compactor may include a chassis structure, a drag link, at least one impact drum of non-round shape which is rotatably mounted to the drag link, and a drop link via which the drag link is connected to the chassis structure, wherein the drop link is pivotally/hingidly connected to both the chassis structure and the drag link at spaced apart positions, and wherein the drop link and drag link form part of the drum mounting arrangement, and
  wherein the measuring arrangement may include two (or more) angle measurement devices, wherein the one angle measurement device is operatively connected between the chassis structure and the drop link, and the other angle measurement device is operatively connected between the drop link and the drag link.

The amount of relative angular displacement between the chassis structure and the drop link, and between the drop link and the drag link, in conjunction with the lengths of the drop link and drag link, can be used in calculating the amount of relative displacement between the at least one drum and the chassis structure.

The angle measurement devices may be a gyroscope, a rotary encoder, an optical flow sensor or an IMU.

The measuring arrangement may include an accelerometer which is mounted on the at least one drum or the drum mounting arrangement, wherein an output of the accelerometer, when double integrated with respect to time, is indicative of the amount of relative displacement between the at least one drum and the chassis structure.

The method may include:
  obtaining dynamic data related to the vertical displacement of the drum of the compactor roller as it travels over the soil; and
  correlating the dynamic data to a scale which indicates the soil strength based on the particular dynamic data.

The scale may have been derived by correlating dynamic data obtained by the vertical displacement of a drum of a compactor roller as it travels over a stretch of soil to data obtained from another well-known soil strength test conducted on the same stretch of soil.

The step of obtaining the dynamic data may include monitoring or measuring the angular velocity of a drum of the compactor roller or a mounting arrangement of the drum which hingidly/pivotally mounts the drum to a chassis structure of the compactor roller, relative to the chassis structure.

The method may include, prior to correlating the data to the scale, processing the data by calculating/estimating the derivative thereof with respect to time, and then correlating the processed data with the scale.

The measuring of the relative displacement may be between:
  an axle assembly of the compactor roller to which the drum is mounted, or a drag link via which the axle assembly is mounted to the chassis; and
  the chassis structure.

The amount of relative displacement may refer to vertical displacement.

The step of obtaining the dynamic data may include measuring the amount of relative displacement between:
  the drum of the compactor roller, or a mounting arrangement of the drum which displaceably mounts the drum to a chassis structure of the compactor roller; and
  the chassis structure or part of the compactor roller which is unaffected by the displacement of the drum relative to the chassis structure.

The method may include processing the dynamic data by calculating/estimating the second derivative thereof with respect to time, and then correlating the processed data with the scale, instead of the dynamic data.

In a further embodiment, the dynamic data may be obtained by measuring the pressure in a pneumatic or hydraulic cylinder which is operatively connected between the mounting arrangement of the compactor roller and the chassis structure, and deriving an indication of the amount of relative displacement between the drum and the chassis structure from the measured pressure.

The mounting arrangement on which the drum is mounted typically includes one or more hinged connections via which the drum is mounted to the chassis structure. In one embodiment, dynamic data may be obtained by measuring the relative angular displacement between the two hingidly connected parts of one, or each, of the hinged connections. In this case, the method may include, prior to correlating the data to the scale, processing the data by deriving the amount of vertical acceleration of the drum of the compactor roller from the measured angular displacement, and then comparing the processed data with the scale.

One type of impact compactor includes a chassis structure, a drag link, at least one impact drum which is rotatably mounted to the drag link, and a link (hereinafter referred to as the "drop link") via which the drag link is connected to the chassis structure, wherein the drop link is pivotally/hingidly connected to both the chassis structure and the drag link at spaced apart positions, and wherein the drop link and drag link form part of a drum mounting arrangement. In this case, the dynamic data may be obtained by monitoring the relative angular displacement between the drag link and the drop link; and/or the drop link and the chassis structure, with the change in angular displacement being indicative of the amount of relative displacement between the impact drum and the chassis structure.

In another embodiment, the dynamic data may be obtained by measuring the strains and/or stresses which the drum and/or the drum mounting arrangement are subjected to during operation. More specifically, the dynamic data may be obtained by measuring the peak strains and/or stresses which the drum and/or the drum mounting arrangement are subjected to during operation.

In another embodiment, the dynamic data may be obtained by measuring the pressure(s) and/or vibration(s) which the drum and/or the drum mounting arrangement are subjected to during operation.

In accordance with a further aspect of the invention there is provided a soil compaction system which includes:

a compactor roller;

a measuring arrangement which includes an inertial measurement unit (hereinafter referred to as "IMU") which is operatively connected to the compactor roller, wherein the arrangement is configured to obtain an indication of the soil strength of soil over which the compactor roller travels during operation, by determining the depth to which the drum penetrates into and depresses the soil over which it travels; and a processor which is operatively connected to the measuring arrangement and which is configured to process data received from the measuring arrangement.

The compactor roller may be a compactor roller as defined above.

The processor and the measuring arrangement may each have a wireless communication unit, which is either connected thereto or forms an integral part thereof, and which allows for wireless communication between the processor and the measuring arrangement.

The system may include at least one graphical user interface (hereinafter referred to as "GUI") which is communicatively connected to the processor and which is configured visually to display processed information received from the processor (e.g. by displaying the information on a screen). The GUI may be located on: the compactor roller (if the roller is self-propelled); a vehicle which tows the compactor roller (if the roller is not self-propelled and needs to be towed); or at an on-site location, remote from the compactor roller. More specifically, the system may include two GUI's, one located on the compactor roller or a vehicle which tows the compactor roller, and the other located at the on-site location.

The system may include a GPS or GNSS unit which is connected to, or forms an integral part of, the measuring arrangement. A wireless communication unit may be operatively connected to the, or each of the, GUI('s) in order to communicate with the processor.

The processor may be configured to send information on the location of the compactor roller, based on coordinate information received from the GPS or GNSS unit, to the GUI('s) which, in turn, may be configured to display the location of the compactor roller relative to a prescribed/pre-determined compactor route for the compactor roller. More specifically, the processor may be configured to send information on the soil strength of the soil over which the compactor roller travels, which is based on coordinate information received from the measuring arrangement, to the GUI('s) which, in turn, are configured to display the information.

The display of the soil strength may be displayed with reference to a specific standard of the soil strength.

The GUI('s) may be configured to use the coordinate information, together with the soil strength information, in order to display a map of a compaction site which is divided into a number of positional regions/cells, wherein each region/cell represents an area of the compaction site (e.g. each region/cell represents 1 $m^2$), wherein the soil strength is displayed for each region/cell.

The GUI('s) may be configured to allow an operator to:
  input certain information regarding compaction specifications of the compaction site, the compaction site layout/boundaries, and/or a planned compaction route, and
  send the said information to the processor.

The processor may be configured to determine a time and/or travel efficient route to cover the whole compaction site, based on the information received from the GUI('s).

The processor may be configured to calculate the average soil strength over each region/cell.

The GUI('s) may be configured to colour code the regions/cells in that different colours represent different levels of soil strength, with reference to a specified standard of soil strength.

The processor may be configured to send visual and/or auditable directions to an operator via the GUI('s) regarding the navigation of a determined/pre-determined compaction route. The processor may be configured to control the operation and navigation of the compactor roller. The on-site GUI may be configured to allow an operator to adjust the compaction route or plan a new compaction route for the compactor roller, during the operation of the compactor roller.

The step of determining the depth to which the drum penetrates into and depresses the ground surface may be conducted continuously/continually (i.e. in real time).

The system may include a storage unit which is connected to the processor and on which data processed from the processor is stored.

The compactor roller may be an impact compactor.

BRIEF DESCRIPTION OF THE DRAWINGS

The invention will now be described, by way of example, with reference to the accompanying diagrammatic drawings. In the drawings.

DETAILED DESCRIPTION OF PREFERRED EMBODIMENT

Figure 1:
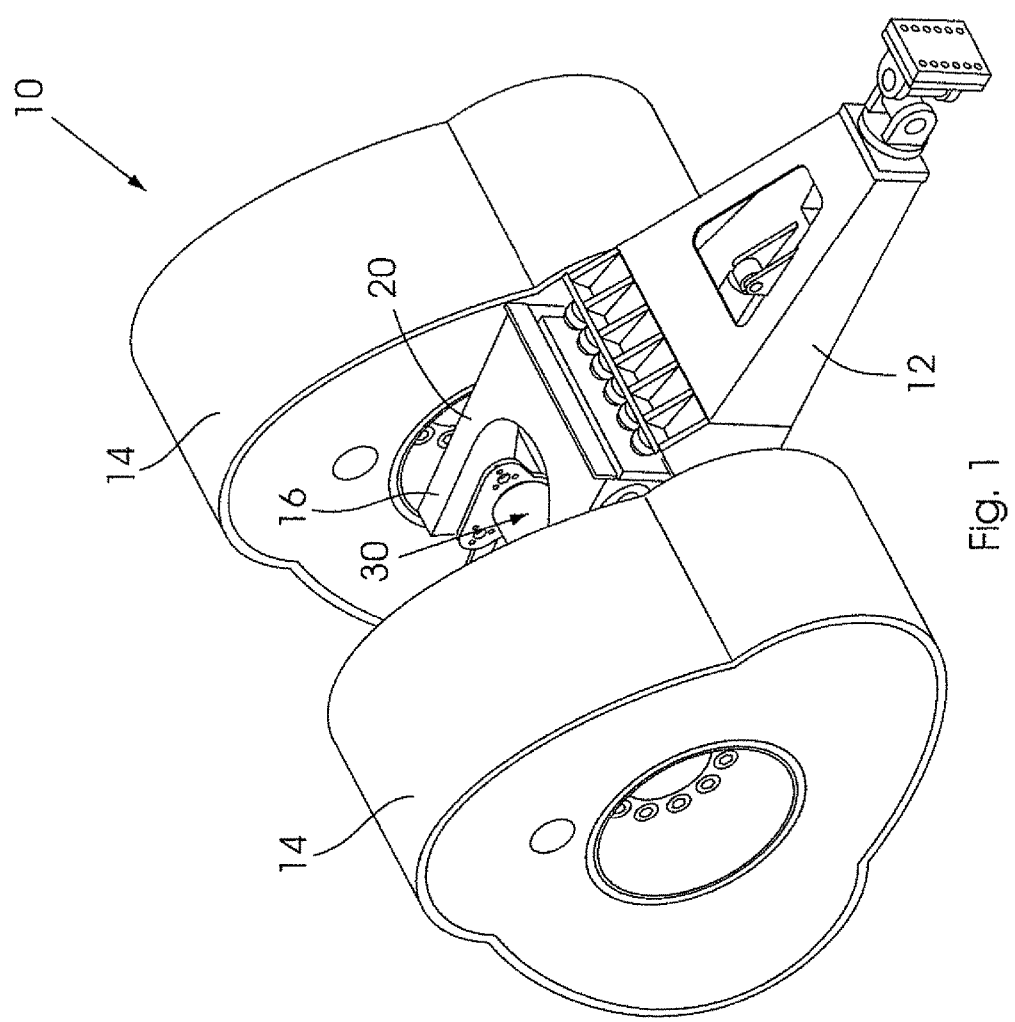
FIG. 1 shows a three-dimensional view of an impact compactor.

The measurement of soil strength is used to determine how strong the soil is, how capable it is of carrying a load and whether or not it is compacted within certain pre-defined specifications. There are a variety of different methods or measurement techniques which can be used to determine soil strength. The inventor believes that the determination of the depth to which a drum of a compactor roller penetrates into and depresses the soil when the compactor roller travels over a soil surface (stroke depth) is an important factor to take into account when determining the soil strength.

The invention provides different, but interrelated, methods or measurement techniques which can be used to determine, estimate or provide an indication of soil strength. An indication of the soil strength can be obtained by:
  using the stroke depth only;
  using the stroke depth together/in conjunction with dynamic data related to the displacement of the drum of the compactor roller as it travels over the soil and correlating the dynamic data to a scale which indicates the soil strength based on the particular dynamic data; or
  using the stroke depth to measure/determine one (or more) of the following measurements/estimations:
    the bearing capacity of the soil over which the impact compactor travels during operation;
    the so-called K-value of the soil over which the impact compactor travels during operation;
    the soil modulus of the soil over which the impact compactor travels during operation; or
    the energy absorbed by the soil during an impact blow.

As mentioned above, bearing capacity, K-value, soil modulus and the energy referred to above are well known terms which are used in the field of impact compaction, each of which can be used to provide an indication of soil strength. The measurements/estimation of the bearing capacity, K-value, soil modulus and energy (referred to above) may be referred to as the direct measurements of soil strength.

In the drawings reference numeral 10 refers generally to a compactor roller in the form of an impact compactor.

Figure 4:
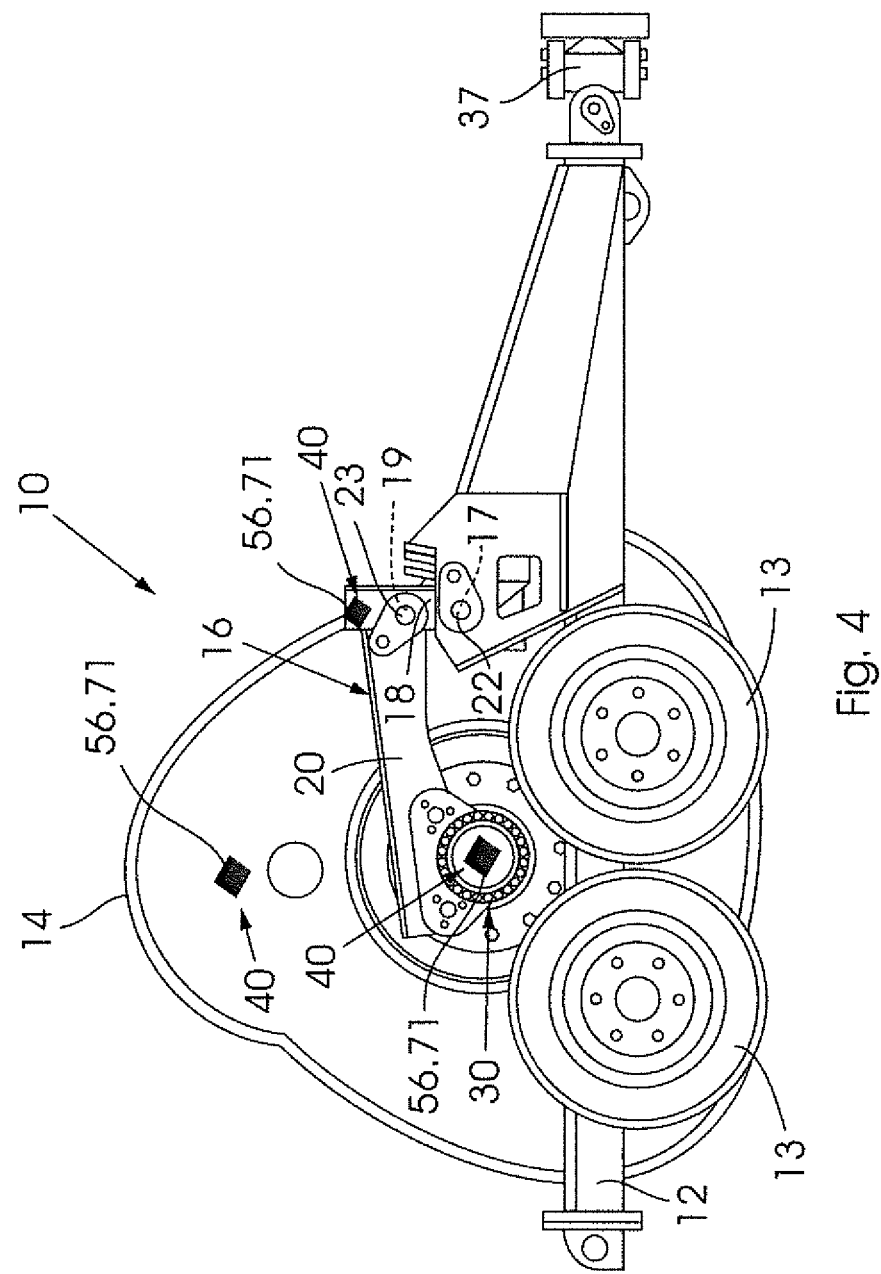
FIG. 4 shows a side view of the impact compactor of FIG. 1, with one of the drums of the impact compactor removed, and where the impact compactor includes a number of gyroscopes.
Figure 6:
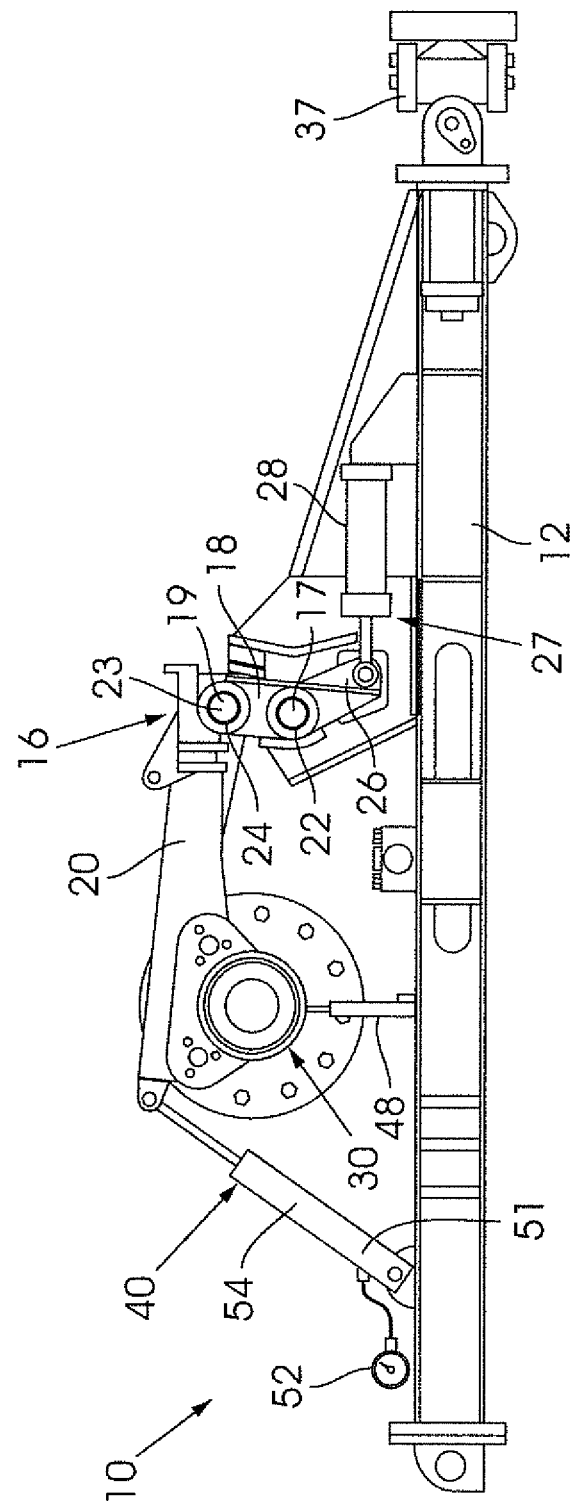
FIG. 6 shows a side view of part of the impact compactor of FIG. 1, which includes a linear encoder and a pneumatic piston-cylinder device.

The impact compactor 10 includes a chassis structure 12; two pairs of wheels 13 on which the chassis structure 12 is supportively mounted; and a drum mounting arrangement 16 on which a pair of non-round impact drums 14 are rotatably mounted (see FIG. 4). The drum mounting arrangement 16 includes a drop link 18 which is pivotally/hingidly mounted to the chassis structure 12 (via a hinged connection 22 having a shaft 17), a drag link 20 which is pivotally/hingidly mounted to the drop link 18 (via a hinged connection 23 having a shaft 19) and an axle assembly 30 via which the drums 14 are rotatably mounted to the drag link 20. More specifically, the drop link 18 includes first and second spaced apart sections 24, 26 (see FIG. 6) between which the pivotal/hinged connection 22 is located, wherein the drag link 20 is pivotally/hingidly connected to the first section 24 and a damping mechanism 27 is pivotally connected to the second section 26, the drop link 18 hence functioning as a first order lever. The damping mechanism 27 includes a damping cylinder 28.

Figure 2:
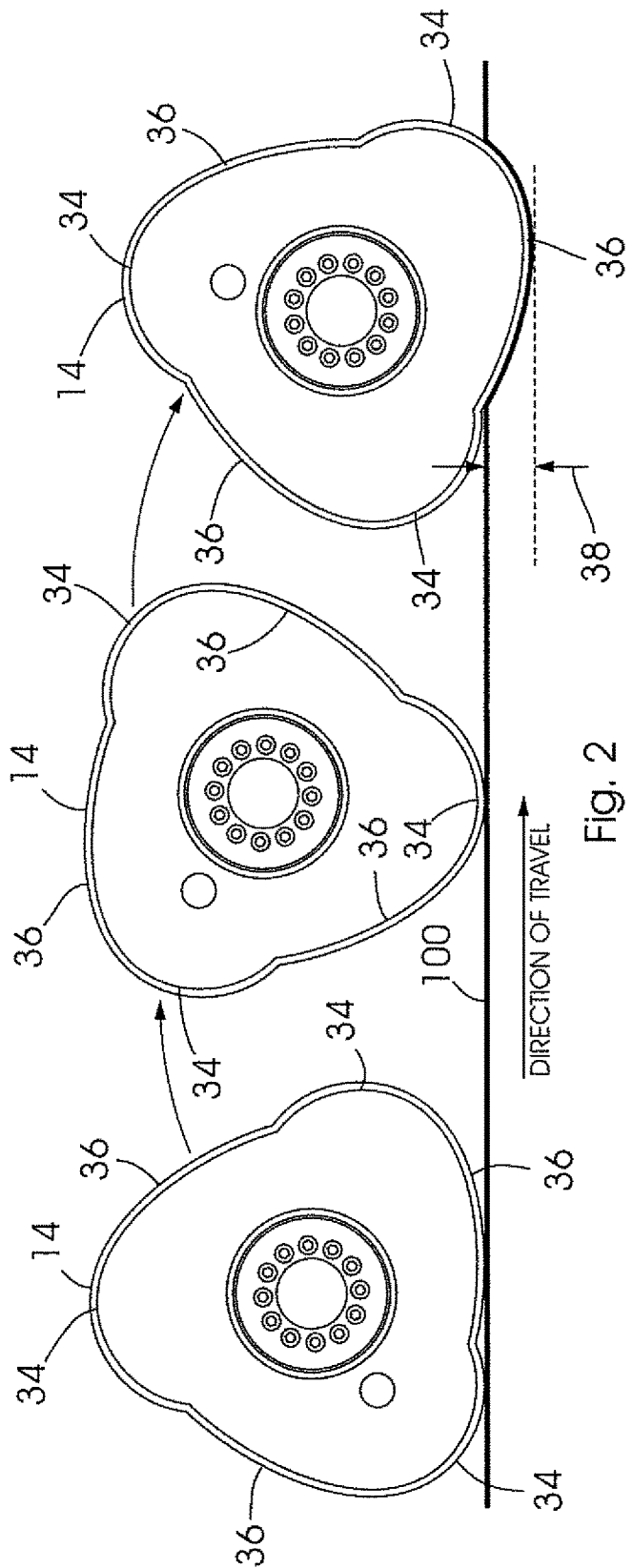
FIG. 2 shows a schematic side view of an impact drum of the impact compactor of FIG. 1 as it rolls and compacts a ground surface over which it travels.
Figure 3:
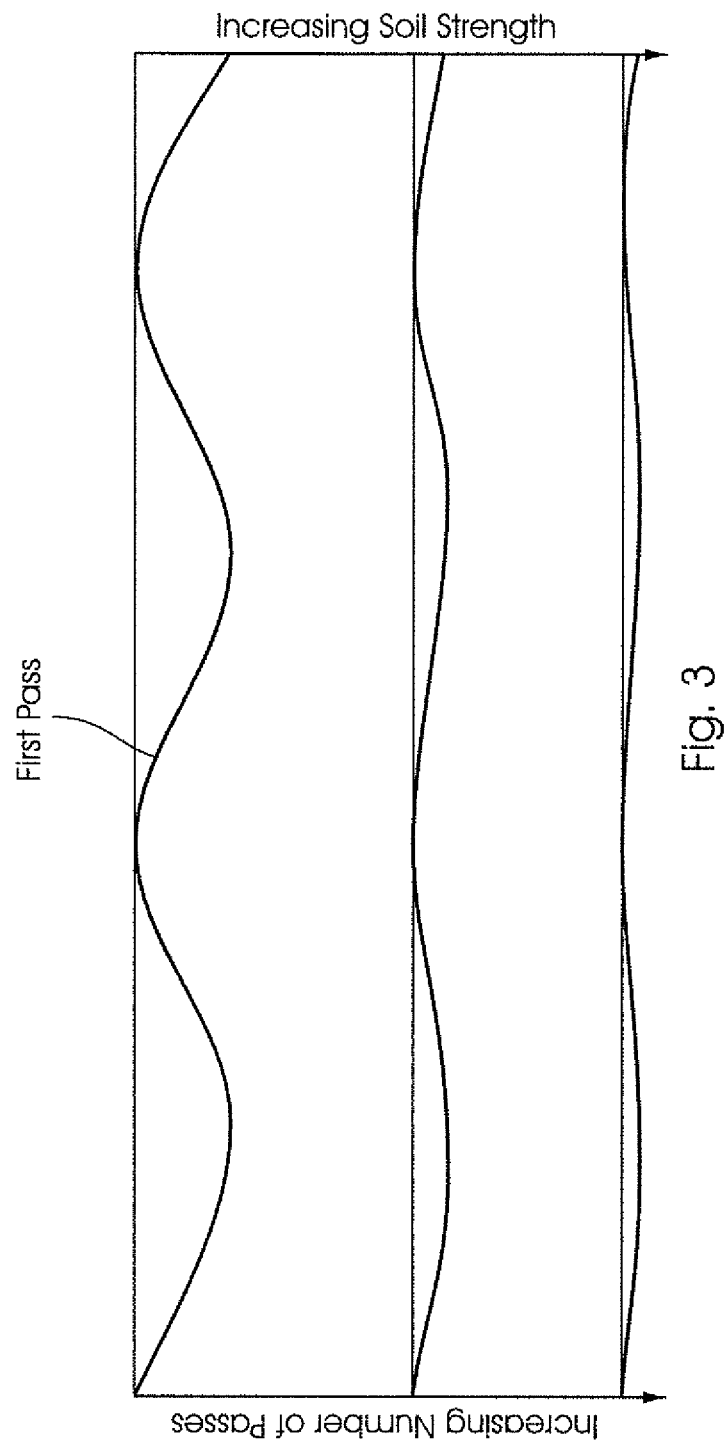
FIG. 3 shows graphical illustration of the effect an impact compactor has on a ground surface.

Due to the non-round shape of the drums 14, it allows them to produce periodic impact blows as they rotate about a common axis and travel over a ground/soil surface 100. Each drum 14 has a number of spaced apart salient portions/points 34 (see FIG. 2) on its radially outer periphery with are each followed by a compacting portion/surface 36 (i.e. an impact surface).

As the impact compactor 10 is towed over the soil surface 100, it rises up on each salient point 34 and then falls forwardly and downwardly as it passes over that point, such that the adjacent compacting surface 36 delivers an impact blow to the soil surface 100. As the drums 14 deliver impact blows, the axle assembly 30 and drag link 20 are displaced upwardly and downwardly relative to the chassis structure 12, and the drop link 18, drag link 20 and chassis structure 12 pivot/hinge relative to each other as the drums 14 travel across the soil surface 100. The drums 14 therefore store potential energy as they rise up on each salient point 34 and then deliver the stored energy as an impact blow. These periodic impact blows compact the soil 100 into a more dense and effective particle arrangement, which reduces air voids and prevents further densification and shear failure of the soil 100. The drums 14 may penetrate into the soil 100 as much as 150 mm or more during an impact blow.

Figure 13:
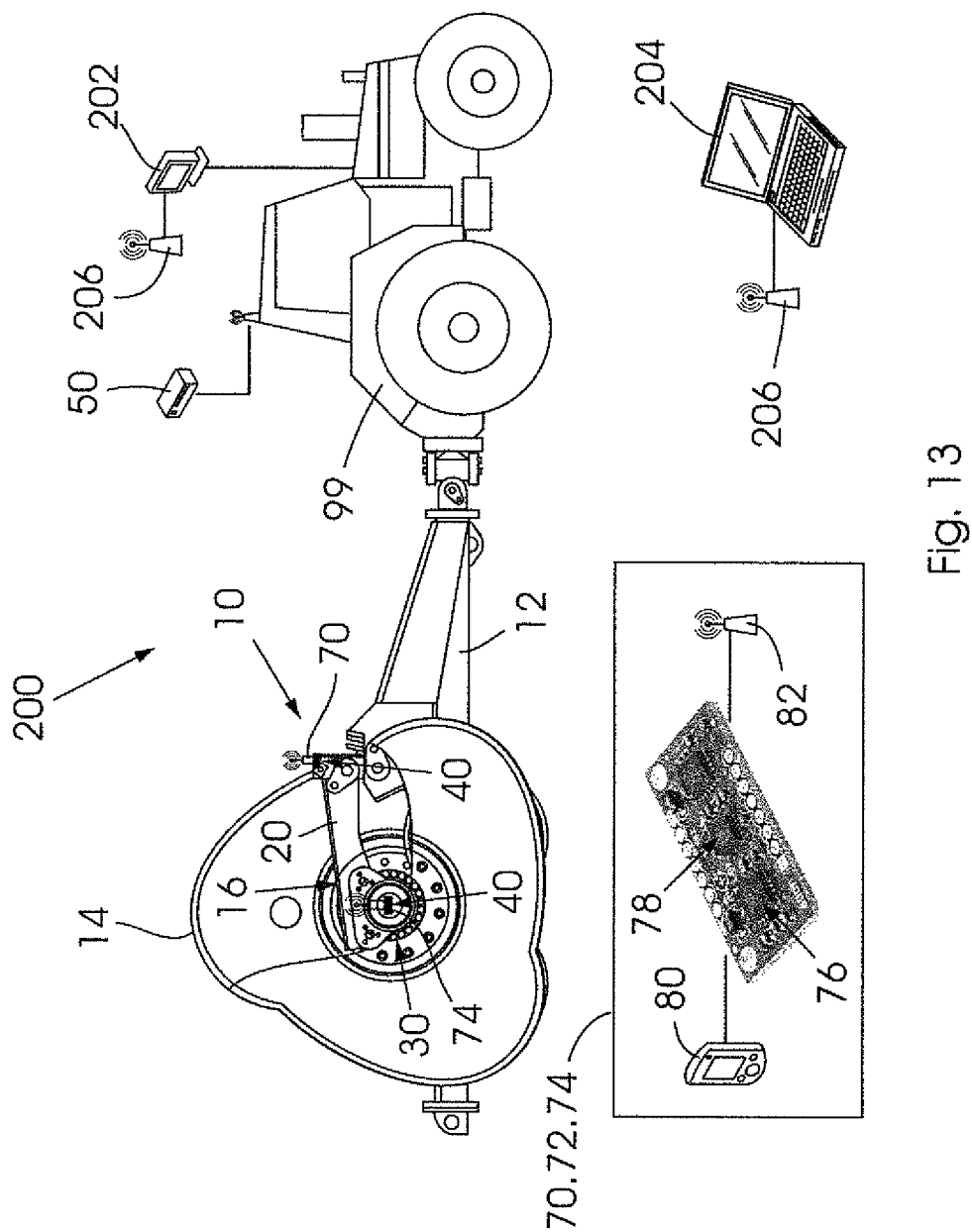
FIG. 13 shows a schematic layout of a soil compaction system in accordance with the invention.

In this example, the impact compactor 10 includes a coupling arrangement 37 which is configured to couple the impact compactor 10 to a tow vehicle, such as a tractor 99 (see FIG. 13). The impact compactor 10 may however also be self-propelled.

Figure 9:
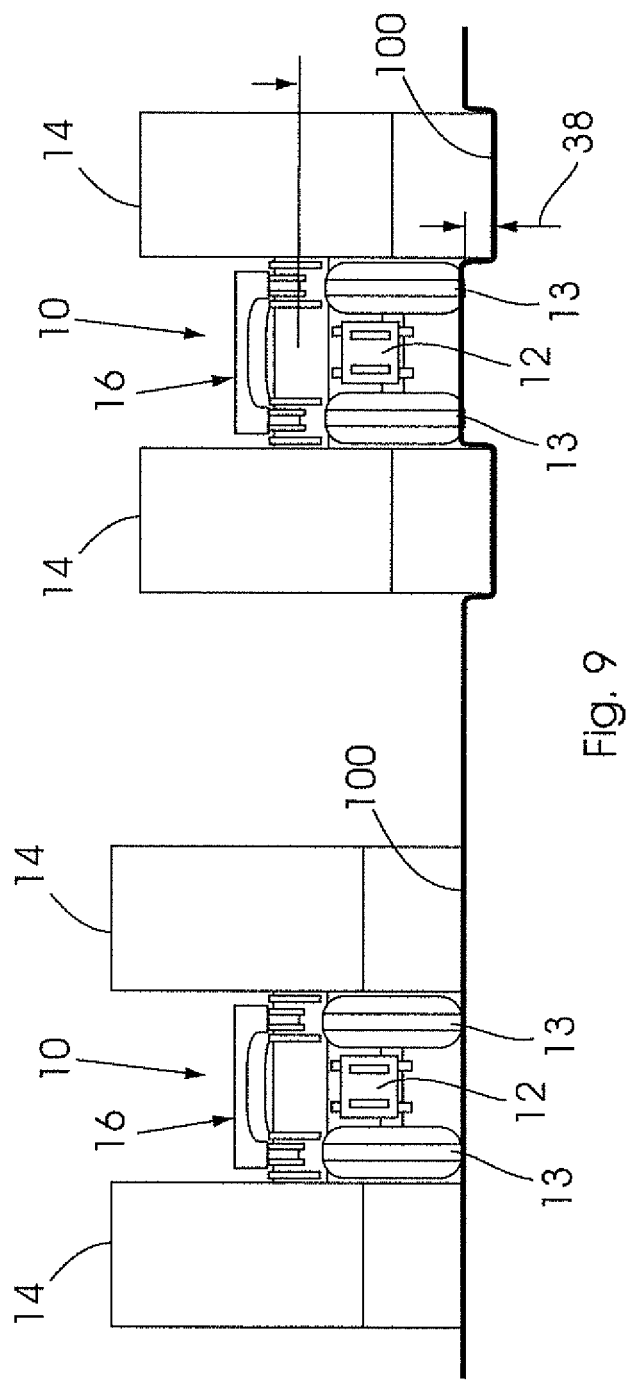
FIG. 9 shows a schematic end view of the impact compactor of FIG. 1 as it compacts a ground surface.

The impact compactor 10 includes a measuring arrangement 40 (see FIGS. 4 and 6) which is configured to obtain dynamic data from the vertical displacement of the drums 14 as they travel over a stretch of soil, wherein the dynamic data can be used to obtain an indication as to the depth to which the drums 14 penetrates into and depresses the soil 100 when the impact compactor 10 travels over the soil surface (i.e. the amount of deformation of the soil surface 100; also hereinafter referred to as the "stroke depth 38" (see FIG. 9)). The penetration depth (i.e. the stroke depth 38) can then be used to obtain an indication of the soil strength of the soil.

Figure 5:
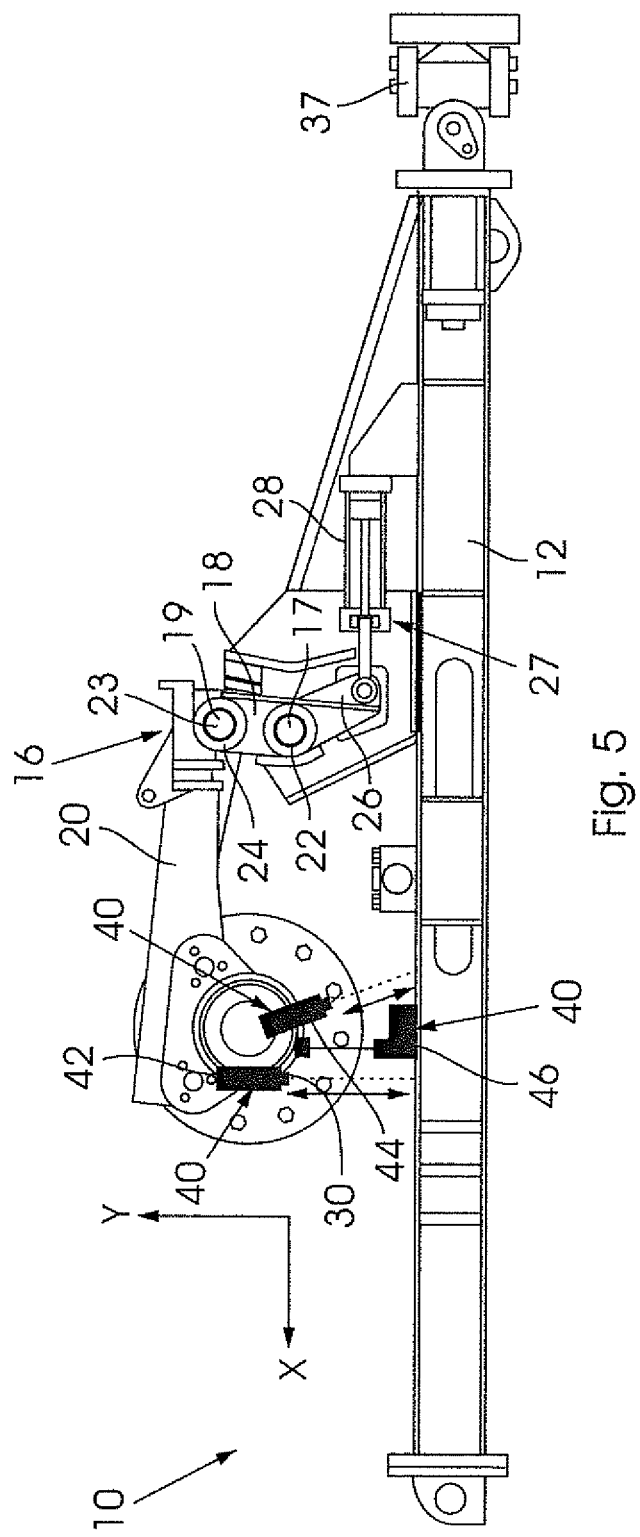
FIG. 5 shows a side view of part of the impact compactor of FIG. 1, which includes a number of distance measuring devices.

The measuring arrangement 40 can include one or more laser, ultrasonic, infrared or similar distance measuring sensors (all types of distance measuring sensors are hereinafter referred to as distance measuring sensors) 42, 44 (see FIG. 5) which are communicatively connected (e.g. by means of a wireless communication network) to a processor 50 (see also FIG. 13). The impact compactor 10 and processor 50 form part of a compaction system 200. The one distance measuring sensor 42 is mounted on the axle assembly 30 and oriented vertically downward towards the chassis structure 12. The other distance measuring sensor 44 is mounted on the axle assembly 30 and is oriented downwardly towards the chassis structure 12 at an oblique angle relative to the distance measuring sensor 42. The processor 50 can then be configured to use measurement data received from the distance measuring sensors 42, 44 in order to measure the change in vertical distance between the axle assembly 30 and the chassis structure 12. The change in vertical distance is accordingly indicative of the stroke depth 38 which, in turn, can be used to obtain an indication of the soil strength of the soil 100. Alternatively, the measuring arrangement 40 includes a linear potentiometer 46 (see FIG. 5) or linear encoder 48 (see FIG. 6) which is mounted between the axle assembly 30 and the chassis structure 12 in order to measure the distance, and more particularly changes in the distance, there between.

Alternatively, the measuring arrangement 40 can include a pneumatic or hydraulic piston-cylinder device 51 (see FIG. 6) which is connected between the drag link 20 and the chassis structure 12, and a pressure meter/gauge 52 which is operatively connected to the piston-cylinder device 51. The pressure gauge 52 is configured to measure the pressure inside a cylinder 54 of the piston-cylinder device 51 and to send the measured data to the processor 50 (e.g. by means of a wireless communication network), wherein the change in pressure inside the cylinder 54 is indicative of the amount of relative displacement between the drag link 20 and the chassis structure 12. The relative displacement, in turn, is indicative of the stroke depth 38, which can again be used to obtain an indication of the soil strength of the soil 100.

Alternatively, the measuring arrangement 40 can include an accelerometer 56 (see FIG. 4) which is mounted on one of the drums 14, the axle assembly 30 or the drag link 20, and which is configured to record the accelerations experienced at a high sampling frequency. The accelerometer 56 is communicatively connected to the processor 50 (e.g. by means of a wireless communication network) in order to send measurement data to the processor 50. In order to obtain the amount of deformation (i.e. the stroke depth 38), the processor 50 is configured to integrate the acceleration data obtained from the accelerometer(s) 56 twice with respect to time. This deformation can then be linked to the stroke depth 38 by filtering out data that does not correspond to the period of impact and interpreting the remaining data to determine the distance from the moment the drums 14 hit/strike the soil (where there will be a sudden deceleration) to the point of maximum penetration.

In order for the processor 50 to integrate only the vertical components of the acceleration data (i.e. to calculate the amount of penetration depth), an IMU (inertial measurement unit) can be used. An IMU includes an arrangement of inertial sensors which is configured to measure the current angle and position of the IMU, as well as raw acceleration and rotation rate inertial data. A typical IMU has 3 orthogonal axes, each axis having an accelerometer and gyroscope. The accelerometer 56 can form part of the IMU or, alternatively, can be separate there from but be connected to the same part of the impact compactor 10 (i.e. one of the drums 14, the axle assembly 30 or the drag link 20). The processor 50 can then use data received from the IMU to calculate the angle in a gravitational reference frame in order to integrate only the vertical components of the acceleration data obtained from the accelerometer 56.

In order to determine the stroke depth, a vertical component of acceleration data obtained from the IMU 70, 72, 74 can be double integrated with respect to time.

Alternatively, the measuring arrangement 40 can include two RTK GNSS (Real Time Kinematic Global Navigation Satellite System) devices mounted at different locations. One device can be mounted on the drums 14, the axle assembly 30 or the drag link 20. The other device can be mounted on the chassis structure 12. The devices measure their vertical positions relative to the ground. The processor 50 can determine the penetration depth by calculating the difference between the two vertical positions measured by the two devices. Alternatively a simple GPS or equivalent device can be used instead of the RTK GNSS device, although this would be less accurate.

Figure 7:
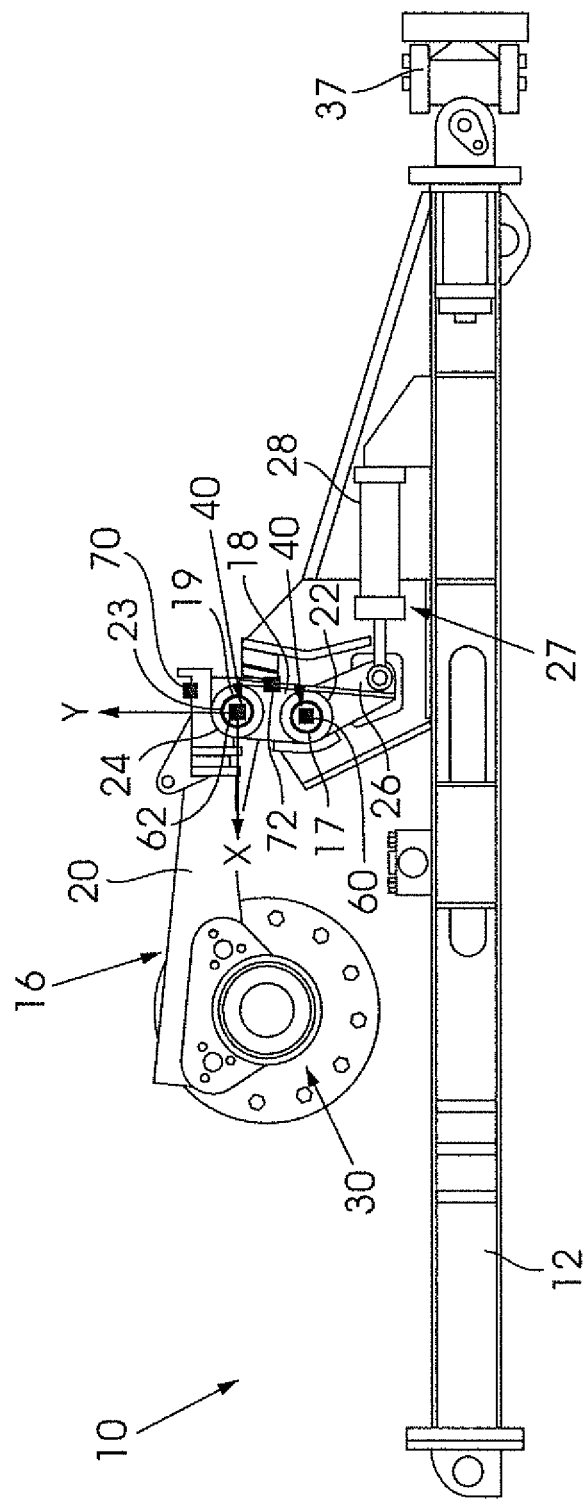
FIG. 7 shows a side view of part of the impact compactor of FIG. 1, which includes two IMU's and two rotary encoders.

Alternatively, the measuring arrangement 40 can include two rotary encoders 60, 62 which are mounted on the shafts 17, 19 and which are communicatively connected to the processor 50 (see FIG. 7). More specifically, the one rotary encoder 60 is mounted between the drop link 18 and chassis structure 12 in order to measure the relative angular displacement there between. In a similar fashion, the rotary encoder 62 is mounted between the drop link 18 and the drag link 20.

Since the lengths of the drop link 18 and drag link 20 are generally known (or can be measured easily), and the linkages between the drag link 20, axle assembly 30, drop link 18 and chassis structure 12 are essentially a four bar linkage system, kinematics can be used to calculate the amount of vertical displacement between the compactor drums 14 and the chassis structure 12. The processor 50 can therefore be configured to use kinematics in calculating the amount of vertical displacement between the drums 14 and the chassis structure 12. In an alternative embodiment, two IMU's can be used, one mounted on the drop link 18 and the other mounted on the drag link 20, in order to measure the relative angular displacements between the drop link 18 and chassis structure 12, and the drop link 18 and drag link 20, respectively. In an alternative embodiment, two optical flow sensors can be used, one mounted on the drop link 18 and the other mounted on the drag link 20, in order to measure the relative angular displacements between the drop link 18 and chassis structure 12, and the drop link 18 and drag link 20, respectively. The zero rate biases of the sensors mentioned above will need to be compensated for.

In order to correlate data received from the measuring arrangement 40 as described above, to soil strength, a scale can be derived by correlating dynamic data obtained from the measuring arrangement 40 of an impact compactor 10 as it travels over a stretch of soil 100 to data obtained from another well-known soil strength test, such as a plate bearing test, conducted on the same stretch of soil 100. The scale can then be used for future reference in correlating dynamic data obtained from other compaction sites.

By using the piston-cylinder device 51 (FIG. 6), the readings from the pressure gauge 52 can be used in conjunction with measurements/readings from a sensor such as the gyroscope 71 (as described below) so that the dynamics of the drums 14 can be taken into account. A data set created from pressure measurements can then be used to correlate the pressure readings to soil strength. In an alternative embodiment, strain sensors located on one of the drums 14, the axle assembly 30 or drag link 20 can be used to measure peak strains and stresses which can be compared to a data set created from stress and strain measurements. In another alternative embodiment, pressure or vibration sensors (located on one of the drums 14, the axle assembly 30 or drag link 20) could be used in the same way as strain sensors with the readings being compared to a data set of pressure and vibration measurements.

In one embodiment, the measuring arrangement 40 includes a gyroscope 71 which is mounted on one of the compactor drums 14, the axle assembly 30 or the drag link 20, and which is configured to measure the rate of rotation of the part of the impact compactor 10 to which it is connected (i.e. the compactor drum 14, the axle assembly 30 or the drag link 20) continuously/continually (see FIG. 4). The gyroscope 71 is communicatively connected (i.e. by means of a wireless communication network) to the processor 50 in order to send measured data to the processor 50. The processor 50 is in turn configured to calculate the derivate of the measured data (with respect to time) and to then correlate the derived data/information to the scale.

Figure 10:
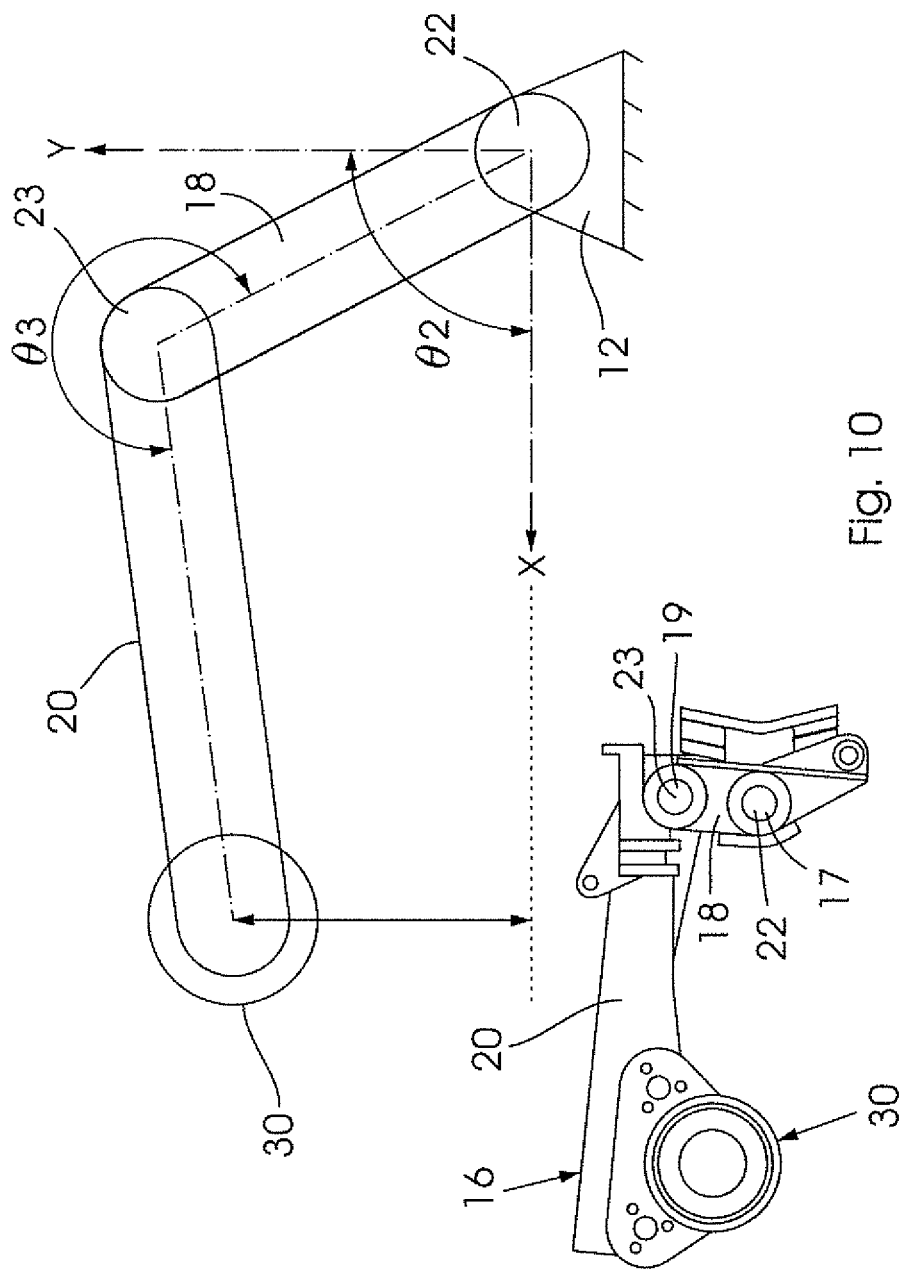
FIG. 10 shows a schematic illustration of the relative angles between a chassis structure, a drop link and drag link of the impact compactor of FIG. 1.

In a similar manner, other sensors such as IMU's, rotary encoders and optical flow sensors 60, 62 could be used to determine the relative angular measurements between the chassis structure 12 and the drop link 18, and the drop link 18 and drag link 20 as well as the angular velocity and angular acceleration of the drop link 18 and the drag link 20. The processor 50 will then accordingly be configured to derive the vertical acceleration of the axle assembly 30 (and drums 14) from the angular measurements which can then be correlated to the scale. The vertical acceleration can be derived by using the linkage system illustrated in FIG. 10.

Figure 11:
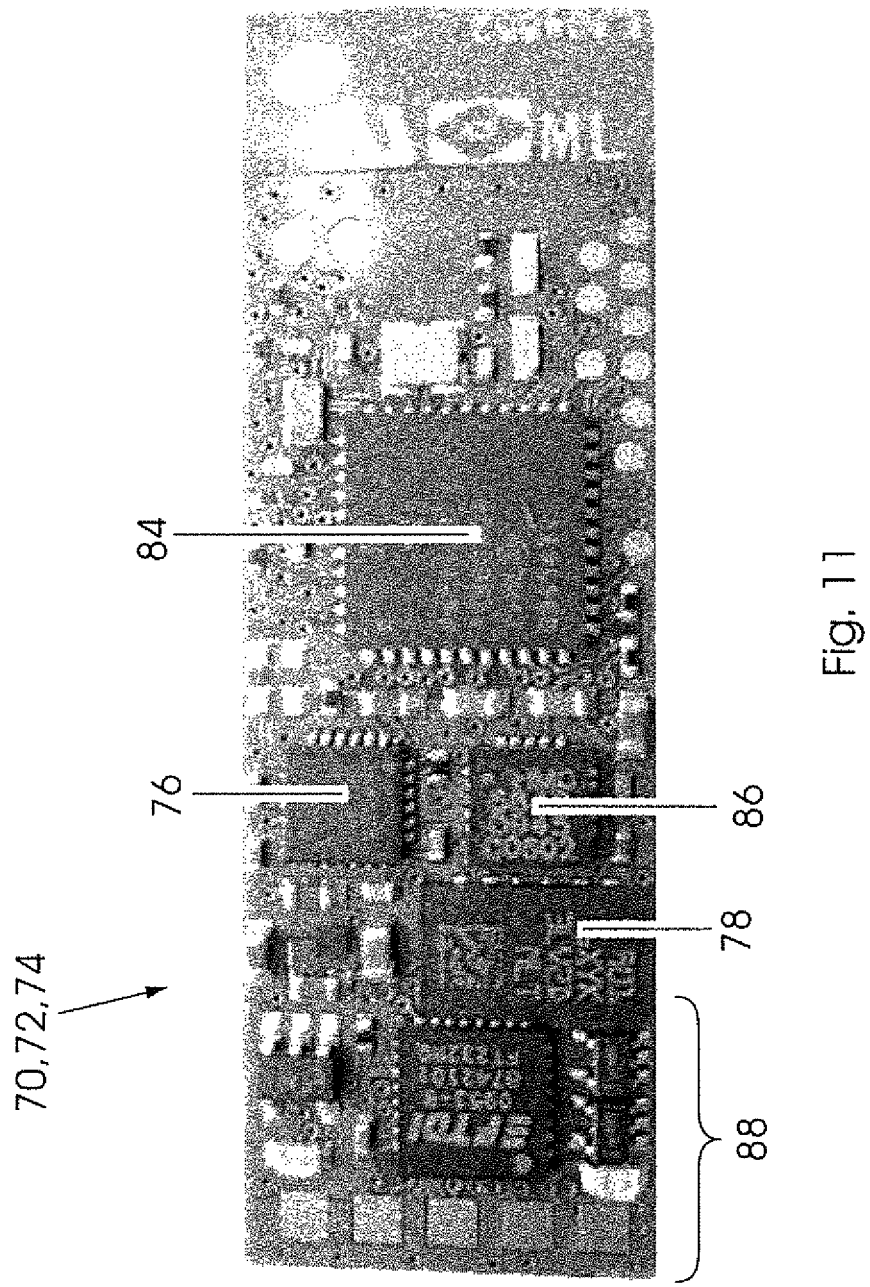
FIG. 11 shows a schematic layout of an IMU.
Figure 12:
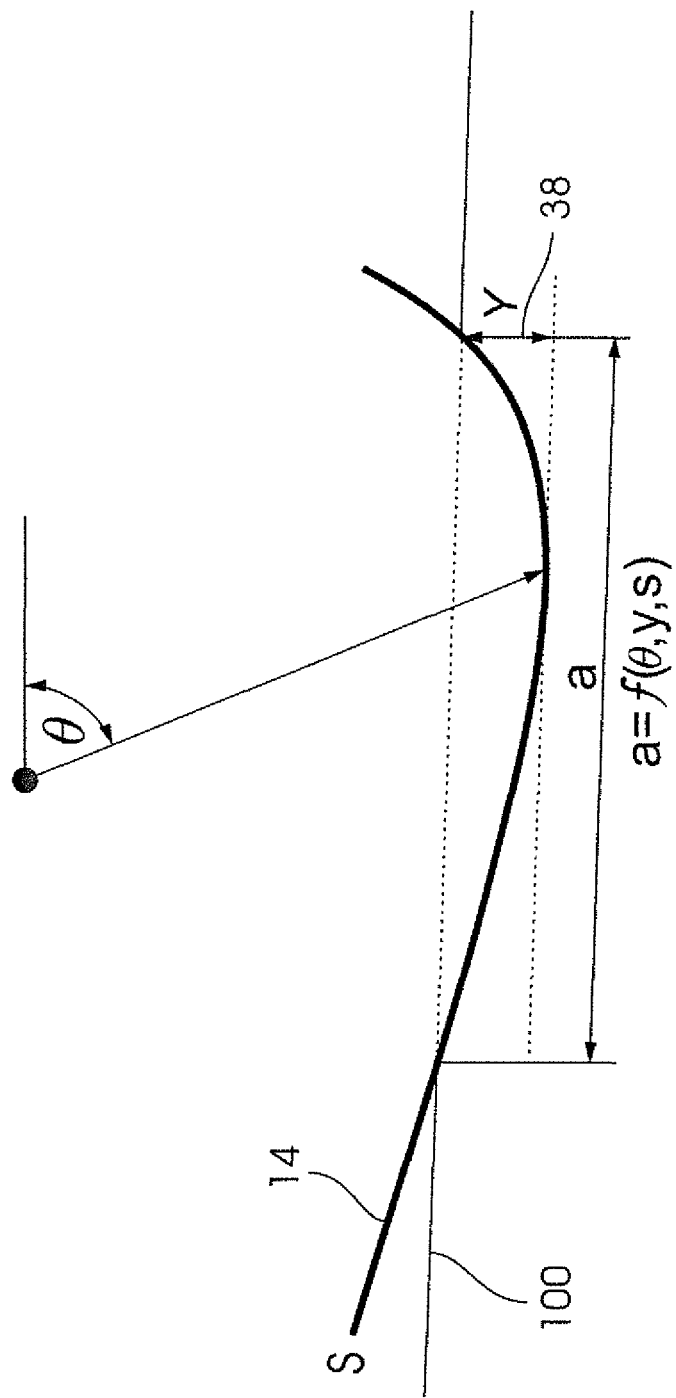
FIG. 12 shows a schematic illustration of a contact area between a drum of the impact compactor of FIG. 1 and a ground surface.

Instead of correlating measurement data to a scale, the system 200 can be used such that soil strength can be measured by means of direct measurements, without the need of deriving a scale beforehand. In order to do so an IMU 70, 72, 74 is mounted on the drag link 20, drop link 18, axle assembly 30 and/or the drums 14 (see FIGS. 7 and 13). Each IMU 70, 72, 74 includes a gyroscope 76, an accelerometer 78, a GPS/GNSS unit 80 and a wireless communication unit 82 which allows for communication between the IMU 70, 72, 74 and the processor 50. The IMU's 70, 72, 74 can therefore send measurement data to the processor 50 for processing. An IMU 70, 72, 74 also typically includes a microcontroller 84, a magnetic field sensor 86, and a USB interface 88 (see FIG. 11).

Figure 8:
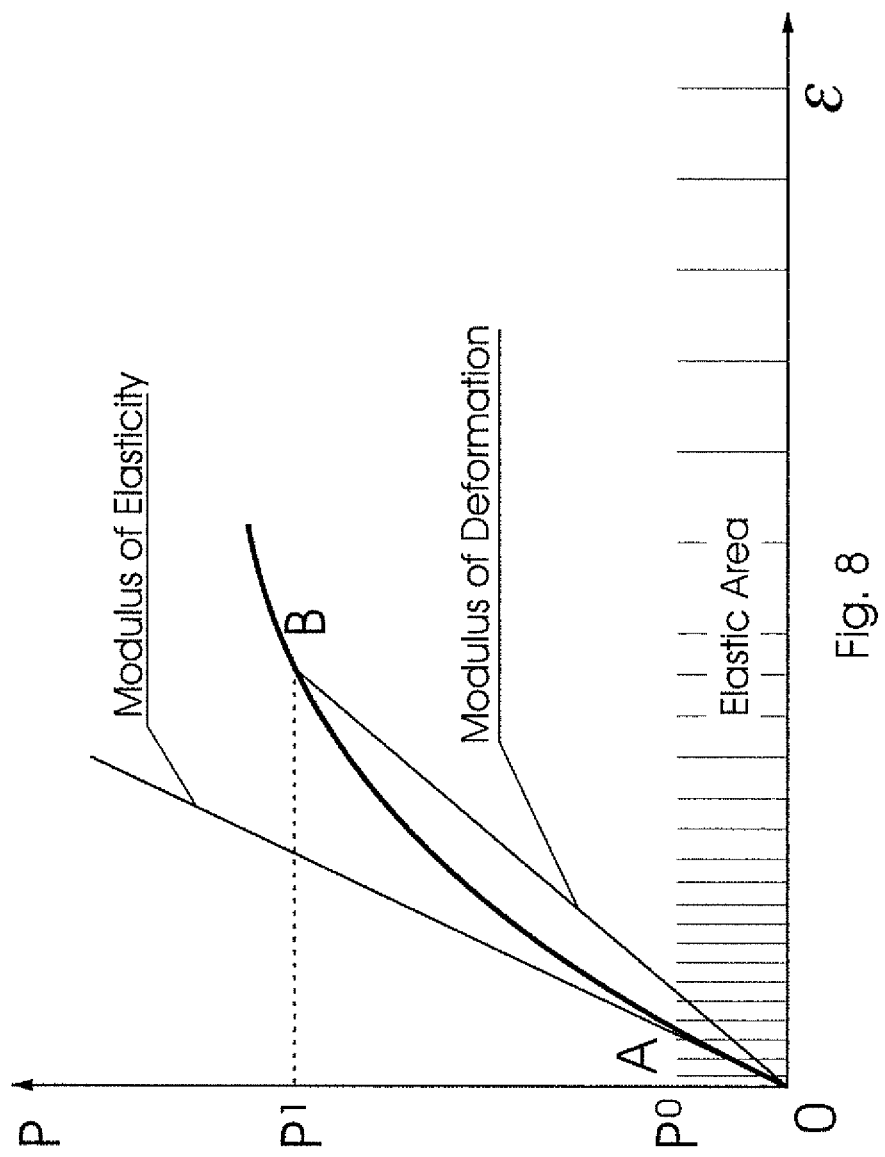
FIG. 8 shows a graphical illustration of a stress/strain curve.

A measurement of soil modulus is highly significant when assessing soil strength. The soil modulus of deformation is the ratio of the applied pressure to strain. Most soils exhibit elastoplastic behaviour under an applied load. The modulus of deformation is the slope of the secant of the stress/strain curve up to the applied load or point of failure B (see FIG. 8). To measure the modulus the applied load at point B needs to be known. This cannot be measured whilst the soil deformation is mostly plastic during an impact blow of the drum 14. As the soil becomes more compacted, the drum 14 will start to show rebound during a stroke. At this stage the portion of the penetration of the drum into the soil (the stroke depth) which is elastic can be measured. The applied pressure (P) is equal to the force (F: measured at point B) divided by the contact area ($A_c$: calculated at point B), $P=F/A_c$. The contact area estimation is described earlier in the specification. For a circular plate, the modulus is then calculated from stroke depth, pressure and Poisson's ratio using Boussinesq's theory as:

$$\Delta z = \frac{\pi P a}{2E}(1 - v^2),$$

where P is the pressure applied, v is Poisson's ratio, $\Delta z$ is the penetration depth, a is the contact area and E is the modulus This will produce a measurement of soil modulus and can be verified by comparison with measurements using current soil modulus measurement devices. Due to the drum 14 not being a circular plate, a more accurate measurement of the modulus can be determined by deriving an equation that suits the drum profile or by finding an empirical correlation. Graphs of applied pressure versus penetration depth could also be produced by using the instantaneous applied force, contact area and penetration depth, in much the same way as produced by plate bearing tests.

The applied pressure and the penetration depth of the drums 14 can be continuously calculated as mentioned above. Using this data, graphs of applied pressure versus penetration depth can be obtained in a similar way as those obtained using plate bearing tests. The K-value is a soil strength measurement determined in plate bearing tests, and it is equal to the applied pressure divided by the penetration depth (measured in $kN/m^3$ or in MPa/m). The K-value is usually calculated for a certain pressure. The K-value can be calculated for different pressures using the graphs produced, which can then be compared to K-values found in plate bearing tests. The graphs could also be used in order to calculate the safe, allowable and ultimate bearing capacity of the soil.

The total energy applied during an impact stroke can be calculated since it is possible to measure both the total change in height of the drums 14, axle assembly 30, drag link 20 and drop link 18, as well as the change in rotational speed of the drums 14 and drag link 20, during an impact stroke. The rotational speed of the drums 14 is measured by the IMU 74 and the rotational speed of the drag link 20 is obtained from the drum 14 geometry and angle (or the IMU 70).

The drum damping rubbers which are mounted between the axle assembly 30 and the drums 14 can be modelled as a spring and damper system in a kinematic model of the impact compactor 10. The material properties of the drum damping rubbers can be used to provide the spring stiffness and damping coefficient for the model. The dynamic measurements determined by the processor 50 can be used in the model to then calculate the deflection of the axle assembly 30 relative to the drum damping rubbers.

The ultimate bearing capacity of soil is the value of the average contact/bearing pressure between the load and the soil which will produce shear failure in the soil. The ultimate bearing capacity of the soil 100 is therefore equal to the average pressure that the drums 14 apply at maximum stroke depth 38 since this is the point where the soil 100 and drums 14 have reached equilibrium and any further increase in pressure will result in further shearing of the soil 100 and a deeper stroke depth. The average pressure that the drums 14 apply to the soil surface 100 at maximum stroke depth 38 is equal to the force applied divided by the contact area.

A mathematical equation can be used in order to calculate the contact area. The mathematical equation requires the following measurements:
 the rotational angle of the drums 14 relative to gravity (i.e. a vertically downward direction);
 the stroke depth 38; and
 the profile of the drum (which is known).

An attitude filter, which is operatively connected to or forms an integral part of, the IMU 70, 72, 74 can be used to reduce electronic noise of readings received from components that form part of the IMU 70, 72, 74 in order to increase the accuracy and reliability of the readings. The attitude filter can be a complementary filter or Kalman filter.

The impact compactor 10 includes an inertial navigation system (hereinafter referred to as "INS") which is operatively connected to the IMU 70, 72, 74, or of which the IMU 70, 72, 74 forms an integral part of. The INS can consist of a RTK GNSS unit in order to achieve very accurate readings. The INS is configured to calculate the position of the IMU 70, 72, 74, and therefore also that part of the impact compactor 10 on which it is mounted, i.e. the drag link 20, drop link 18 or axle 32. In order to do so, the INS combines inertia data from the IMU 70, 72, 74 with lower frequency measurements of position obtained from the GNSS unit 80. In this embodiment a custom algorithm can be implemented to compute the travel of the drums 14 during their stroke travel. Whenever inertial sensors are used (e.g. inertial sensors of the IMU 70, 72, 74), it is necessary to have a low frequency measurement to correct the drift of the inertial sensors. The INS will perform this correction by using the calculated compactor drum 14 angle measurement (see above). This is possible since the drum profile is known and there is an angle of rotation of the drums 14 that will correspond to zero vertical velocity of the axle assembly 30 (i.e. the tipping point of the drums 14 before they fall downward (see FIG. 2)). This measurement need not be precise, but need only be accurate when averaged over multiple cycles. For example, IMU's that track a gravity component/vector for angle estimation are able to reject very high accelerations due to device motions, provided the acceleration is not sustained and averages out to gravity over longer periods (this value is tuned based on the system dynamics, but a few seconds is typical).

With the measurement of the vertical velocity of the drums 14, the acceleration measurements of the IMU 70, 72, 74 are integrated in the vertical direction with respect to time in order to compute the position of the drums 14. The angle of the drums 14 should be known at all times in order to integrate only the components of acceleration in the vertical direction. This is done by transforming the accelerations in an IMU frame of reference (often referred to as the "body frame") to a gravity vector frame of reference (often referred to as the "navigation frame") by multiplying the acceleration vector by a Direction Cosine Matrix. The other reference that is used by the INS is the ground level detection for each stroke or impact blow. This is sensed by a rapid change in acceleration and/or rotation rate of the drums 14 as they first make contact with the soil surface 100. This can also be achieved with other additional sensors which are mounted on one of the drums 14, chassis structure 12, drag link 20 or axle assembly 30 and which are configured to detect when the drums 14 strike/hit the soil surface 100 during an impact blow. In one example, the sensor can be a microphone which is configured to detect/identify the sound created when the drums 14 strike/hit the ground during an impact blow. In other examples, a strain gauge, a pressure sensor or a capacitive electrode which is configured to sense the presence of the soil surface 100 may be used.

By deriving and using a kinematic model of the impact compactor 10 together with acceleration data obtained from the IMU 70, 72, 74, the force applied can be calculated. The force of interest to be used in calculating the bearing capacity would be the peak force calculated during the drum blow.

As mentioned above, the IMU 70, 72, 74 and processor 50 form part of a soil compaction system 200 which also includes two graphical user interfaces 202, 204 (hereinafter referred to as "GUI's"), each of which is connected to a wireless communication unit 206 in order to allow for communication (e.g. by using Bluetooth technology) between the GUI's 202, 204 and the processor 50. The one GUI 202 is mounted on a tractor 99 (or on the impact compactor 10 if it is self-propelled) which tows the impact compactor 10, while the other GUI 204 is located at an on-site location, remote from the tractor 99.

As mentioned above, the processor 50 performs all the data manipulation and calculations required which is then sent through as useful measurements and information to the GUI's 202, 204 for display purposes. The system 200 also includes a storage device (not specifically shown) on which the processor 50 stores the calculated information. The processor 50 typically functions as a closed loop control system.

The GUI's 202, 204 are configured to display the current location of the impact compactor 10 relative to a prescribed compaction route by using the position data received from the GNSS unit 80. A graphical representation of the degree of soil strength achieved with reference to specified standards will be recorded in the form of a map. The map is customisable in order to allow for the display of a selection of properties within a grid of colour coded positional cells, wherein each cell represents an area of the compaction site (e.g. 1 m$^2$).

Prior to the commencement of compaction, a user could input certain information via one of the GUI's 202, 204, such as site compaction specifications, compaction site boundaries and a planned route. This information is sent to the processor 50 which, through the use of an algorithm, can calculate automatically the most efficient route to uniformly cover the whole compaction site. As the impact compactor 10 travels over the compaction site, the measured soil strength for each cell is averaged for all the measurement data collected within that cell. The averaged soil strength calculated for each cell is then compared to the specified standard value, and the cell is colour coded based on the comparison. More specifically, the cells could be colour coded according to the colours of a rainbow, wherein so-called "hot" colours such as red and orange indicate poor compaction while so-called "cool" colours such as green and blue indicate that the specification standard has been met.

The processor 50 can be configured to provide a navigation function in which it sends navigation instructions to the GUI('s) 202, 204 which in turn provides an operator with visual and audible navigational instructions for following the calculated pre-determined route. The processor 50 can be configured to send an instruction message to the GUI's 202, 204 (which in turn communicates the instruction (e.g. visually and/or audibly) to an operator) instructing the operator to speed up or slow down the tractor speed. Alternatively, the processor 50 can be configured to control the tractor 99 (or impact compactor if self-driven) automatically. The GUI 202, 204 is configured to allow an operator or a site-engineer to modify the specified standards of soil strength and, when necessary, adjust/plan new routes for the impact compactor 10 to follow during operation. This will give a site-engineer the ability to communicate with the impact compactor operator without having to halt the compaction progress, thereby maximising the efficiency of the compaction process. The processor 50 can further be configured to communicate to an operator, via the GUI's 202, 204, visually and/or audibly that the required soil strength has been achieved.

In one embodiment the impact compactor 10 and processor 50 can be configured to allow the impact compactor 10 to be controlled remotely in order to eliminate the use of an operator on the impact compactor. In this case, the desired route and the speed of the impact compactor 10 could be pre-programmed into the processor 50 for a specific site. A GNSS unit, such as the GNSS 80 of the IMU 70, 72, 74, can be used to track the progress of the impact compactor 10 and make sure that it stays on course. Alternatively, a separate GNSS unit can be used. The system 200 could be configured to determine the surroundings of the impact compactor 10 and whether or not there are obstacles nearby that might need to be avoided. The processor 50 will be able to plan optimal routes and control the towing vehicle 99 to follow the programmed route, stopping if something is in the way and/or avoiding hazardous obstacles The impact compactor 10 and system 200 provides an innovative way of determining whether the soil over an entire compaction site has indeed been sufficiently compacted. The impact compactor 10 and system 200 further provides soil strength measurements of the entire compaction site, without the need of carrying out currently used conventional soil tests, such as plate bearing tests, during or after the compaction process, which may be tedious, time-consuming and expensive.

The Inventor believes that the impact compactor 10 and system 200 will provide a better, faster, more convenient and more reliable method for determining whether the compacted soil has sufficient strength to support whatever load it may be required to carry in the future.

The invention claimed is:

1. A method of obtaining an indication of the soil strength of soil over which an impact compactor travels, the method including:
   determining, when the impact compactor travels over a soil surface, a stroke depth to which a non-round impact drum of the impact compactor penetrates into and depresses the soil during application of an impact blow by the impact drum to the soil surface, wherein a duration of the impact blow begins when an impact face of the impact drum strikes the soil surface and ends when the impact face lifts away from the soil surface.

2. The method of claim 1, wherein the step of determining the stroke depth to which the impact drum penetrates into and depresses the soil includes measuring, by using a measuring arrangement, the amount of relative displacement between:
   the impact drum of the impact compactor, or a mounting arrangement of the impact compactor which displaceably mounts the impact drum to a chassis structure of the impact compactor, and
   a reference/datum point.

3. The method of claim 2, wherein the reference/datum point is the chassis structure or part of the impact compactor which is unaffected by the displacement of the impact drum relative to the chassis structure.

4. The method of claim 3, wherein the step of determining the stroke depth to which the impact drum penetrates into and depresses the soil includes measuring, by using a distance measuring device, the distance between:
   an axle assembly of the impact compactor on which the impact drum is mounted, or a drag link via which the axle assembly is mounted to the chassis structure, wherein the axle assembly and the drag link form part of the mounting arrangement; and
   the chassis structure.

5. The method of claim 1, wherein a mounting arrangement of the impact compactor on which the impact drum of the impact compactor is mounted and which displaceably mounts the impact drum to a chassis structure of the impact compactor, includes one or more hinged/pivotal connections via which the impact drum is connected to the chassis structure of the impact compactor, and wherein the method includes monitoring, by using an angular measurement device/arrangement, the relative angular displacement between two hingedly connected parts of one, or each, of the hinged/pivotal connections.

6. The method of claim 5, wherein the impact compactor includes the chassis structure, a drag link, at least one impact drum of non-round shape which is rotatably mounted to the drag link, and a drop link via which the drag link is connected to the chassis structure, wherein the drop link is pivotally/hingedly connected to both the chassis structure and the drag link at spaced apart positions, and wherein the drop link and the drag link form part of a drum mounting arrangement, wherein the method includes:
   measuring, by using an angular measurement device/arrangement, the relative angular displacement between the drag link and the drop link; and/or the drop link and the chassis structure, with the change in angular displacement being indicative of the amount of relative displacement between the impact drum and the chassis structure, which, in turn, is indicative of the stroke depth to which the impact drum of the impact compactor penetrates into and depresses the soil.

7. The method of claim 6, which includes, by using a processor, utilising the known lengths of the drop link and the drag link together with data obtained from the angular measurement device/arrangement, in order to obtain an indication of the amount of relative displacement between the impact drum and the chassis structure, which, in turn, is indicative of the stroke depth to which the impact drum of the impact compactor penetrates into and depresses the soil.

8. The method of claim 1, wherein the step of determining the stroke depth to which the impact drum penetrates into and depresses the soil includes:
   measuring the pressure in a cylinder of a pneumatic piston cylinder device which is operatively connected between a mounting arrangement of the impact compactor on which the impact drum of the impact compactor is mounted and which displaceably mounts the impact drum to a chassis structure of the impact compactor, and the chassis structure, and
   deriving, by using a processor, an indication of the amount of relative displacement between the impact drum and the chassis structure from the measured pressure, which, in turn, is indicative of the stroke depth to which the impact drum of the impact compactor penetrates into and depresses the soil.

9. The method of claim 1, wherein the step of determining the stroke depth to which the impact drum penetrates into and depresses the soil includes:
   measuring, by using an accelerometer, the amount of acceleration which the impact drum of the impact compactor is subjected to during an impact blow; and
   deriving, by using a processor, an indication of the amount of relative displacement between the impact drum and a chassis structure of the impact compactor to which the impact drum is displaceably mounted from the measured acceleration, which, in turn, is indicative of the stroke depth to which the impact drum of the impact compactor penetrates into and depresses the soil.

10. The method of claim 1, wherein the step of determining the stroke depth to which the impact drum of the impact compactor penetrates into and depresses the soil during an impact blow, when the impact compactor travels over the soil surface includes:

obtaining data from an inertial measurement unit ("IMU") which is mounted on the impact drum of the impact compactor or a mounting arrangement on which the impact drum is mounted and which displaceably mounts the impact drum to a chassis structure of the impact compactor, and determining, by using a processor, the stroke depth by utilising the data.

11. An impact compactor which includes:

a chassis structure;

at least one non-round impact drum which is rotatably mounted to the chassis structure via a drum mounting arrangement, wherein the drum mounting arrangement allows displacement of the at least one impact drum relative to the chassis structure such that the at least one impact drum is displaced upwardly and downwardly relative to the chassis structure as the impact compactor travels along a soil surface; and a measuring arrangement, which is operatively connected to the chassis structure and/or the drum mounting arrangement, and which obtains an indication of the soil strength of soil over which the impact compactor travels when the impact compactor travels over the soil surface by determining a stroke depth to which the at least one impact drum penetrates into and depresses the soil surface during application of an impact blow by the impact drum to the soil surface, wherein a duration of the impact blow begins when an impact face of the impact drum strikes the soil surface and ends when the impact face lifts away from the soil surface.

12. The impact compactor of claim 11, wherein the measuring arrangement includes an IMU which is mounted on the impact drum or the drum mounting arrangement.

13. The impact compactor of claim 11, wherein the measuring arrangement includes at least one distance measuring device which is:

mounted on the drum mounting arrangement and directed towards the chassis structure or part of the impact compactor which is unaffected by the displacement of the at least one drum relative to the chassis structure; or mounted on the chassis structure or part of the impact compactor which is unaffected by the displacement of the at least one drum relative to the chassis structure and directed towards the drum or the drum mounting arrangement.

14. A soil compaction system which includes:

an impact compactor;

a measuring arrangement which includes an inertial measurement unit which is operatively connected to the impact compactor, wherein, when the impact compactor travels over the soil surface, the measuring arrangement obtains an indication of the soil strength of soil over which the impact compactor travels during operation by determining a stroke depth to which a non-round impact drum of the impact compactor penetrates into and depresses the soil during application of an impact blow by the impact drum to the soil surface, wherein a duration of the impact blow begins when an impact face of the impact drum strikes the soil surface and ends when the impact face lifts away from the soil surface; and a processor which is operatively connected to the measuring arrangement and processes data received from the measuring arrangement.

15. The system of claim 14, wherein the impact compactor comprises:

a chassis structure;

at least one impact drum which is rotatably mounted to the chassis structure via a drum mounting arrangement, wherein the drum mounting arrangement is configured to allow displacement of the at least one impact drum relative to the chassis structure such that the at least one impact drum can be displaced upwardly and downwardly relative to the chassis structure as the impact compactor travels along a ground surface; and a measuring arrangement, which is operatively connected to the chassis structure and/or the drum mounting arrangement, and which is configured to obtain an indication of the soil strength of soil over which the impact compactor travels when the impact compactor travels over a soil surface, by determining the stroke depth to which the at least one impact drum penetrates into and depresses the ground surface over which the impact compactor travels during operation.

16. The method of claim 10, wherein the step of determining the stroke depth to which a drum of the impact compactor penetrates into and depresses the soil during an impact blow includes determining a vertical component of acceleration data obtained from the IMU.

17. The method of claim 16, further comprising double integrating the vertical component of the acceleration data with respect to time.

18. The method of claim 17, wherein the step of determining a vertical component of acceleration data obtained from the IMU includes transforming acceleration data from the IMU from an IMU frame of reference to a gravity vector frame of reference by multiplying an acceleration vector by a direction cosine matrix.

19. The impact compactor of claim 12, further including a processor which is operatively connected to the measuring arrangement and which is configured to process data received from the measuring arrangement, wherein the processor is configured to determine the stroke depth to which the drum of the impact compactor penetrates into and depresses the soil during an impact blow by:

determining a vertical component of acceleration data obtained from the IMU; and double integrating the vertical component of the acceleration data with respect to time.

20. The impact compactor of claim 19, wherein the processor is configured to transform acceleration data from the IMU from an IMU frame of reference to a gravity vector frame of reference by multiplying an acceleration vector by a direction cosine matrix.

* * * * *